US007012538B2

(12) United States Patent
Peck et al.

(10) Patent No.: US 7,012,538 B2
(45) Date of Patent: Mar. 14, 2006

(54) HEATING ELEMENT CONDITION MONITOR

(75) Inventors: Kevin B. Peck, Sonora, CA (US); Noel H. Johnson, Sonora, CA (US); Thomas J. Berdner, Sonora, CA (US)

(73) Assignee: MRL Industries, Sonora, CA (US)

( * ) Notice: Subject to any disclaimer, the term of this patent is extended or adjusted under 35 U.S.C. 154(b) by 0 days.

(21) Appl. No.: 10/619,561

(22) Filed: Jul. 16, 2003

(65) Prior Publication Data

US 2004/0075567 A1 Apr. 22, 2004

Related U.S. Application Data

(63) Continuation-in-part of application No. 10/196,160, filed on Jul. 17, 2002.

(51) Int. Cl.
*B60Q 1/00* (2006.01)
(52) U.S. Cl. ........................ 340/640; 219/505; 219/506
(58) Field of Classification Search ................ 340/640; 219/497, 484, 505, 506, 552, 553; 392/407
See application file for complete search history.

(56) References Cited

U.S. PATENT DOCUMENTS

| | | | |
|---|---|---|---|
| 4,518,850 A | * | 5/1985 | Grasso ........................ 219/505 |
| 4,549,073 A | | 10/1985 | Tamura et al. |
| 4,891,497 A | * | 1/1990 | Yoshimura ................... 219/241 |
| 4,979,134 A | | 12/1990 | Arima et al. |
| 5,270,520 A | * | 12/1993 | Barzilai et al. ............. 219/501 |
| 5,280,422 A | | 1/1994 | Moe et al. |
| 5,552,998 A | * | 9/1996 | Datta .......................... 702/99 |
| 5,629,869 A | | 5/1997 | Johnson et al. |
| 5,754,451 A | | 5/1998 | Williams |
| 5,864,773 A | | 1/1999 | Barna et al. |

* cited by examiner

*Primary Examiner*—Jeffery Hofsass
*Assistant Examiner*—Jennifer Stone
(74) *Attorney, Agent, or Firm*—Drinker Biddle & Reath LLP

(57) ABSTRACT

A method for monitoring the condition of a heating element involving installing the heating element in a location and setting the initial composition $C_i$ of the material as a reference baseline at an initial time $T_i$ corresponding to said installation of the heating element. Data is then collected reflecting the subsequent composition $C_s$ of the heating element material after a subsequent time $T_s$ at the installed location and any change in the material composition of the heating element between $T_i$ and $T_s$ is monitored. An alarm is sent when the change reaches a threshold value indicating a possible failure condition. According to one embodiment, an impedance monitor is provided that calculates and compares impedance at the required levels of accuracy to determine changes in material composition. The impedance monitor, or portions thereof can be embedded within a microcontroller for increased portability and functionality.

36 Claims, 19 Drawing Sheets

| Time | Hot Resistance | Cold Resistance | Resistance Ratio | Remaining Alloy |
|---|---|---|---|---|
| $T_1$ | $R_{h1}$ | $R_{c1}$ | $X_{R1}$ | $A_{R1}$ |
| $T_2$ | $R_{h2}$ | $R_{c2}$ | $X_{R2}$ | $A_{R2}$ |
| $T_3$ | $R_{h3}$ | $R_{c3}$ | $X_{R3}$ | $A_{R3}$ |
| ⋮ | ⋮ | ⋮ | ⋮ | ⋮ |
| $T_n$ | $R_{hn}$ | $R_{cn}$ | $X_{Rn}$ | $A_{Rn}$ |
| 400 | 402 | 404 | 406 | 408 |

FIG. 4

HEATING ELEMENT CONDITION MONITOR

CROSS-REFERENCE TO RELATED APPLICATION

This application is a continuation-in-part of and claims priority from U.S. nonprovisional patent application Ser. No. 10/196,160, filed Jul. 17, 2002, the contents of which are incorporated herein by reference.

FIELD OF THE INVENTION

The present invention relates to a method and apparatus for monitoring characteristics of a material to determine if that material has undergone a sufficient change in the monitored characteristics to indicate that a failure has occurred, or that an impending failure is about to occur. More particularly, the present invention relates to a method and apparatus for monitoring the physical and electrical characteristics of materials used as heating elements to indicate that there has been a failure or a partial failure of the heating elements, and/or to provide an indication of a heating element's condition and risk of pending failure.

BACKGROUND OF THE INVENTION

Many industrial applications and business enterprises use heating elements and assemblies containing heating elements (e.g., furnaces and ovens) in various manufacturing processes. For example, the semiconductor industry uses these heating elements and assemblies to heat silicon wafers and other substrate materials that are used in the integrated circuit fabrication process. Wafers are thin slices of material (generally a semi-conductor) used to manufacture microelectronic device (e.g., integrated circuits). The heating elements are used to generate the required temperatures in the heating cycles used in the associated manufacturing processes. For example, it is common to utilize temperatures in the range of 300–1400° C. in common industrial applications.

Because of the thermal stresses caused by temperature cycling degradation attributed to changes in temperature from cold to hot and hot to cold, heating elements generally degrade with use and can eventually fail. If the failure occurs unpredictably and at an inopportune time, serious consequences can result. For example, the failure of a heating element can occur while devices such as a batch of semi-conductors, are being heated in a furnace. Consequences of the failure of a heating element used in such a process can include the loss of an entire batch of semiconductor product that is in the oven at the time of the heating element failure. A failure can result in lost revenue, delayed shipments to customers, and a general inability to meet promised and expected yield rates for manufactured components.

It would be very useful, therefore, to be able to determine or predict when a material that makes up a heating element is about to fail. One way of addressing this problem is to conduct a preventative maintenance program by monitoring the amount of time that an item subject to such failures (e.g., a heating element) has been used. After the passage of a predetermined period of time, the item can be replaced prior to an expected potential failure. However, it is often difficult to predict a life expectancy or reliability of heating elements. Moreover, there can be a great deal of variability in the amount and quality of use of such heating elements, and differences in the quality of such items can be diverse as well. In addition, other factors, such as intrinsic or elemental contamination of the materials, can also adversely affect the useful life of such a device.

Accordingly, in view of the foregoing, it would be useful to provide a system and method that predicts or anticipates the potential failure of materials, such as heating elements, due to thermal cycling degradation, so that appropriate corrective action can be pursued prior to the failure of such devices. The present invention achieves the foregoing objectives and solves additional problems, by way of monitoring the condition of heating elements and other devices that can contain materials that experience degradation due to thermal cycling, and providing an indication of a possible pending failure. The present invention is advantageous in that it is easily installed, and can be readily retrofitted to existing equipment. Furthermore, the present invention is minimally invasive, such that it does not adversely compromise the reliability of existing equipment.

SUMMARY OF THE INVENTION

The present invention, therefore, achieves the above objectives by way of a system and method for monitoring materials exposed to repeated thermal cycles. According to an exemplary method of the present invention, the condition of material used in thermal cycling (e.g., heating elements) is monitored by selecting at least one characteristic of the material for monitoring. The initial value of the selected characteristic is measured at an initial time, and is maintained as a reference base line. Subsequently, characteristics of the material, including the selected characteristic, are monitored to determine any changes that occur over time, and subsequent values for the selected characteristic are measured and stored. The subsequent values of the selected characteristic are compared against the initial values of the selected characteristic, or against the reference base line of the characteristic, and changes in the selected characteristic are monitored. Once the changes in the selected characteristic exceed a predetermined threshold level, a signal is sent to a decision making authority, and serves as a notification that the change in the selected characteristic has surpassed a predetermined threshold level. In accordance with an embodiment of the present invention, at least one of the characteristics monitored is the electrical resistance or impedance of the material. However, those skilled in the art will recognize that other characteristics can also be monitored including, for example, a voltage value, an instantaneous voltage value, a current value, a temperature value, or a combination of these.

Another method for monitoring the condition of an electrical current-carrying heating element involves measuring the initial composition $C_i$ of a material as a reference baseline at an initial time $T_i$. The initial time $T_i$ can, for example, correspond to a time shortly after the installation of a heating element and prior to its use in any thermal cycling processes. Data regarding the subsequent composition $C_s$ of the heating element at a subsequent time $T_s$ is collected. Variations between the initial composition $C_i$ data and the subsequent composition $C_s$ data are monitored and compared, and a determination is made as to whether or not a predetermined threshold level of change in the composition has taken place. If it is determined that the change in the composition from $C_i$ to $C_s$ has reached or exceeded a predetermined threshold level, then a signal is sent to a decision making authority notifying that the threshold level has been reached.

In accordance with an embodiment of the present invention, a system is provided that monitors the condition of the heating element. The apparatus measures at least one component of the initial composition $C_i$ of the material that makes up the heating element at an initial time $T_i$ as a reference baseline characteristic. The initial composition $C_i$ can correspond, for example, to the heating element's composition at a time shortly after the installation of the heating element. The apparatus comprises a means for collecting data reflecting the subsequent composition $C_s$ of the heating element material at a subsequent time $T_s$. A means for comparing changes between the subsequent composition $C_s$ of the material and the initial composition $C_i$ of the material is provided. A means for signaling a decision making authority when the changes reach or exceed a threshold value indicating a possible failure condition is also provided by the system of the present invention.

According to an exemplary embodiment of the present invention, the method and apparatus of the present invention can make use of a heating element made from an alloy having a composition by weight of approximately 72.2% iron (Fe), 22.0% chromium (Cr), and 5.8% aluminum (Al).

Exemplary embodiments are directed to a method for monitoring the condition of a material, including determining a reference baseline for at least one characteristic of a material; monitoring the at least one characteristic of the material across time and/or temperature; comparing the monitored characteristic against the reference baseline; and initiating a signal when the difference between the monitored characteristic and the reference baseline exceeds a predetermined value.

An additional embodiment is directed to a method for monitoring the condition of a heating element, including determining a first graphical representation of a characteristic of a heating element as a reference baseline; setting a threshold level of graphical change for the characteristic; collecting data reflecting the condition of the characteristic of the heating element material after an interval; converting the collected data to a second graphical representation; comparing the difference between the first and second graphical representations against the threshold level of graphical change; and sending a signal to a decision making authority when the difference reaches or exceeds the threshold level.

A further embodiment is directed to an apparatus for monitoring the condition of the material, including means for determining an initial composition $C_i$ of a material as a reference baseline at an initial time; means for collecting data reflecting a subsequent composition of the material after a specified time interval; means for setting a threshold level of change in the subsequent composition from the initial composition; means for monitoring a change in the composition of the material after the interval has passed; and means for sending a signal to a decision making authority when the monitored change has reached or exceeded the threshold level.

As will be described below, a signal can be generated when the alloy of the heating element approaches or reaches a failure zone, which in accordance with an embodiment of the present invention has been determined to occur when the percentage content of aluminum has been depleted to approximately 2.5% of the total composition of the alloy. This percentage value can be determined from a change in resistance characteristics of the alloy. For example, a change in the resistance ratio $X_R$ of the resistance of the alloy at hot temperatures $R_h$ versus the resistance of the alloy at cold temperatures $R_c$ can provide a useful indicator regarding when the aluminum of the alloy making up the heating element has been depleted below a threshold level and that a potential failure can be imminent. The ratio $X_R$ is described by Equation (1) below:

$$X_R = \frac{R_h}{R_c} \qquad (1)$$

where $R_h$ is the resistance of the alloy at a hot temperature, $R_c$ is the resistance of the alloy at a cold temperature, and $X_R$ is the temperature-based ratio of the two resistances, or the temperature coefficient of resistance for the alloy. Alternately, in other exemplary embodiments, a normalized resistance of the alloy can be used to determine the condition of the heating element.

In accordance with an embodiment of the present invention wherein the heating element is made from an alloy containing approximately 72.2% iron, 22.0% chromium, and 5.8% aluminum by weight, the resistance ratio $X_R$ of the alloy at 1,400 degrees Celsius is approximately 1.044, meaning that the resistance at hot temperatures of the alloy is approximately 4.4% greater than the resistance of the alloy at cold temperatures. However, as aluminum is depleted from the alloy during heating and cooling cycles, the resistance within the alloy at cold temperatures decreases notably. For example, when the percentage content of aluminum contained within the alloy that makes up the heating element has been depleted to approximately 2.5% of the total alloy, the normalized resistance of the heating element decreases from 1.0 to approximately 0.822. Similarly, as the resistance at cold temperature is reduced from the depletion of the aluminum, the resistance ratio $X_R$ increases to approximately 1.27, meaning that the resistance at hot temperatures is approximately 27% greater than the resistance at cold temperatures within the aluminum-depleted alloy.

The resistance and the resistance ratio $X_R$ can be readily ascertained by way of various measurements, such as resistance or voltage and/or current measurements, a threshold value for a maximum acceptable deviation from a baseline value can be readily set, and a signal can be generated whenever that threshold is reached or exceeded. Thus, by way of a notification signal generated in such an instance, a heating element can be replaced before failure due to damage to the element's alloy that occurs as a result of thermal cycling degradation.

These and other features of the invention are explained in greater detail hereinafter with reference to an exemplary embodiment of the invention illustrated in the accompanying drawings, wherein like elements are designated by like reference numerals.

BRIEF DESCRIPTION OF THE DRAWINGS

FIG. 4 is a diagram of a relational database used for tracking variable values in accordance with an embodiment of the present invention.

DETAILED DESCRIPTION

Many different materials and alloy compositions exist that can be used to construct heating elements. The choice of the types of materials and alloy compositions used can depend upon the particular application with which the heating element is to be used, design requirements, economic considerations and other considerations. However, as will be appreciated by those skilled in the art, similar techniques to those described herein could be used with other alloys to achieve similar results.

One type of wire alloy used to make up a heating element is an alloy consisting essentially of iron (Fe), chromium (Cr), and aluminum (Al), which is commonly referred to as an Fe/Cr/Al alloy. In the following description, for the purpose of illustration and not limitation, the present invention will be described in connection with an exemplary embodiment that uses the Fe/Cr/Al alloy to make a heating element. Those skilled in the art will recognize that other alloys and compositions can be used without departing from the spirit and scope of the present invention. Additionally, those skilled in the art will recognize that rather than using a wire alloy heating element, various other types of heating elements can be used with the present invention. For example, a heating element can be constructed using a patterned heat source, such as a semiconducting alloy on an insulating substrate that integrates current voltage and/or temperature sensors into the pattern. Such design variations can be encompassed within the spirit and scope of the present invention, and are not intended to be excluded from the present invention by way of the description of the wire alloy heating element exemplary embodiment.

Figure 1:
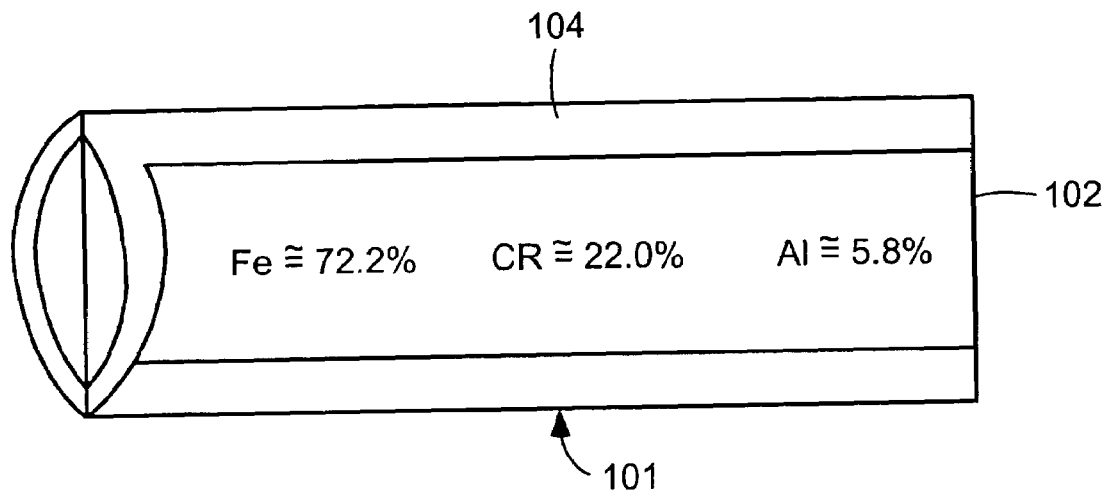
FIG. 1 is a diagram of an exemplary wire alloy used to make up the core of a heating element.

An exemplary wire alloy heating element 101 is illustrated in FIG. 1. This wire alloy heating element is made up of an Fe/Cr/Al alloy core 102, and has a protective oxide layer 104 that surrounds the alloy core 102. Generally, this type of wire heating element has a useful operating temperature range of up to about 1400° C., thereby making it well suited for a broad range of industrial applications. The ability of the wire alloy heating element 101 shown in FIG. 1 to operate at such high temperatures is aided by the protective aluminum oxide layer 104 that forms on the surface of the alloy core 102. This layer 104 forms when the alloy is heated to temperatures above about 1000° C. in the presence of oxygen (e.g., in ambient air). The aluminum oxide layer 104 has a mechanical characteristic of providing an outer shell that has a much higher strength at high temperatures (i.e., the "hot strength") than an Fe/Cr alloy by itself. Additionally, the oxide layer 104 also provides a protective barrier that shields the iron in the core 102 from the oxidizing effect of the surrounding ambient atmosphere on the alloy 102.

Typically, a wire alloy heating element 101 is used in a variety of industrial applications, wherein multiple heating and cooling cycles of the heating element 101 are required. For example, material to be processed by the wire alloy heating element 101 (i.e., a work product) can be loaded into a furnace heated by the heating element within a controlled atmosphere. This work product can be, for example, contained in a process liner and then placed in a heating chamber at a lower temperature. The temperature of the heating chamber or furnace, and consequently the temperature of the work product, is then gradually increased to a target temperature, or temperature range, at which a specific reaction occurs to achieve a desired outcome. The atmosphere of the furnace can be controlled for a period of time to sustain the desired reaction, and after the desired effect has been achieved, a protective atmosphere is restored and the temperature is reduced to a range that will no longer support the reaction. Once the temperature has been reduced to a temperature that will not support any further reaction, the work product can be removed from the furnace. This process can be repeated many times for different batches of work product. The constant heating and cooling of the heating element 101 subjects the heating element itself to significant stress.

Figure 2:
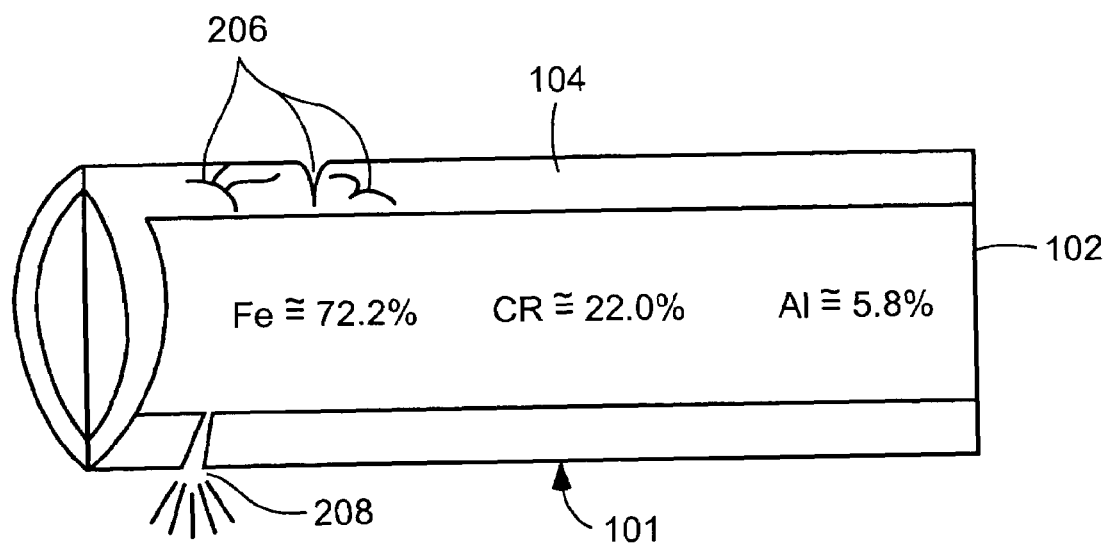
FIG. 2 is a diagram of a wire alloy of the type shown in FIG. 1, showing thermal cycling degradation.

During the portion of the thermal cycle at which temperatures are high, the thermal expansion characteristics of the aluminum oxide layer 104 and the core materials 102 of the alloy are different, subjecting the heating element to significant stress. For example, typical values of the coefficient of thermal expansion for the core materials 102 in the range of 20–1000° C. (i.e., within standard operating temperatures) would be about $15 \times 10^{-6}$ per degree Celsius, while the coefficient of thermal expansion for the aluminum oxide layer 104 would be about $8 \times 10^{-6}$ per degree Celsius for the same temperature range. Because of the differing thermal expansion characteristics of the oxide layer 104 and the core 102, the repeated heating and cooling cycles creates a physical stress on the heating element wire 101. FIG. 2 illustrates some of the consequences of these stresses associated with the thermal cycles on the heating element wire 101.

As can be seen in FIG. 2, the heating element wire 101 is exhibiting various cracks 206 and a fissure 208 in the protective aluminum oxide layer 104 (commonly referred to as a scale). While both the cracks 206 and the fissure 208 reduce overall performance of the heating element wire 101, of particular concern are fissures, such as the fissure 208, where the entire aluminum oxide layer 104 has been broken through. The exposure to atmosphere via the cracks 206 and the fissure 208 can result in undesirable iron and chromium compounds (e.g., oxides, nitrides, etc.) that consume the alloy components, including the aluminum content, and change the both the metallurgical and the electrical properties of the heating element wire. These undesirable compounds lead to an inhomogeneous resistance, sub-standard performance, and premature failure. Specifically, as the metallurgical composition of the alloy core 102 changes, the core's conductivity can be greatly reduced, and both the current flowing through the core 102 and the corresponding heating power of the heating element 101 can be greatly reduced.

In particular, the formation of cracks 206 and fissures 208 in the protective aluminum oxide layer 104 of the heating element wire 101 degrades the wire 101 both metallurgically and physically. From a metallurgical perspective, exposure of the alloy core 102 of the wire 101 to the atmosphere through the cracks 206 and fissures 208 causes the rebuilding of the damaged sections of the aluminum oxide layer 104, thereby resulting in the depletion of aluminum from the core 102. As aluminum from the core 102 is depleted to rebuild a section of the protective aluminum oxide layer 104, the resistance ratio $X_R$ of the heating element wire is found to increase, because the resistance of the changed alloy 102 is decreased at cold temperatures. Because of this direct relationship, one can determine if the percentage of aluminum content of the alloy has changed from a prior baseline reference measurement by measuring the resistance of the alloy 102 and comparing the resistance and/or the resistance ratio to a baseline resistance value.

Figure 9:
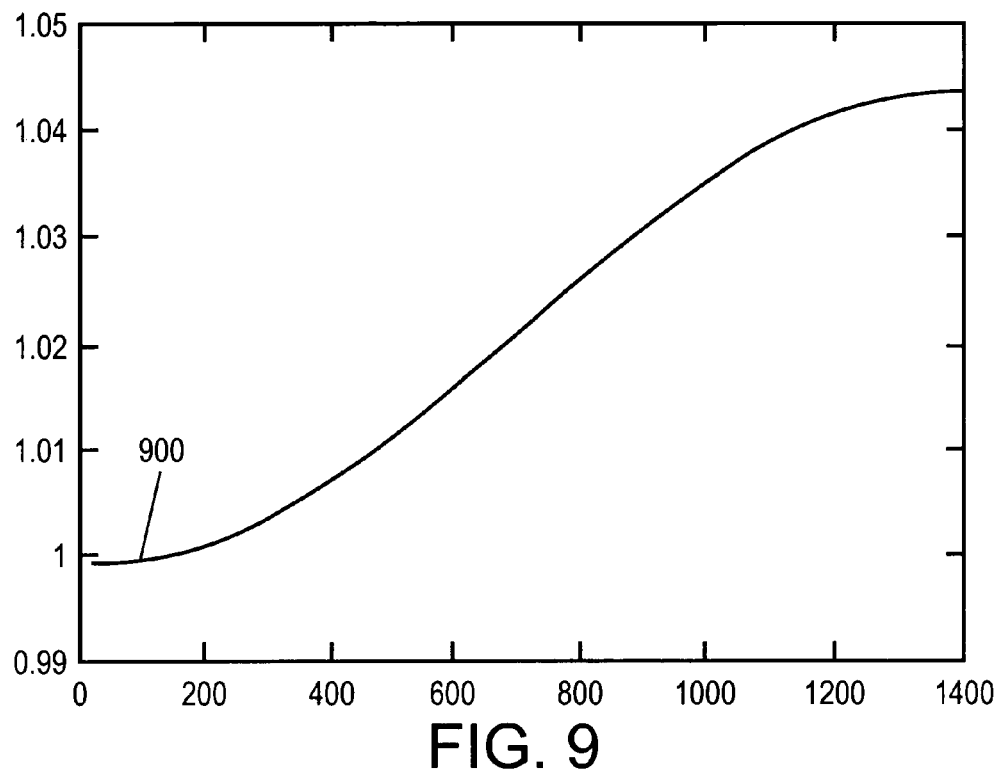
FIG. 9 is a diagram of a temperature resistance curve at various temperatures, for an element comprised of approximately 5.8% aluminum, normalized to 1.0 at 20° C.
Figure 10:
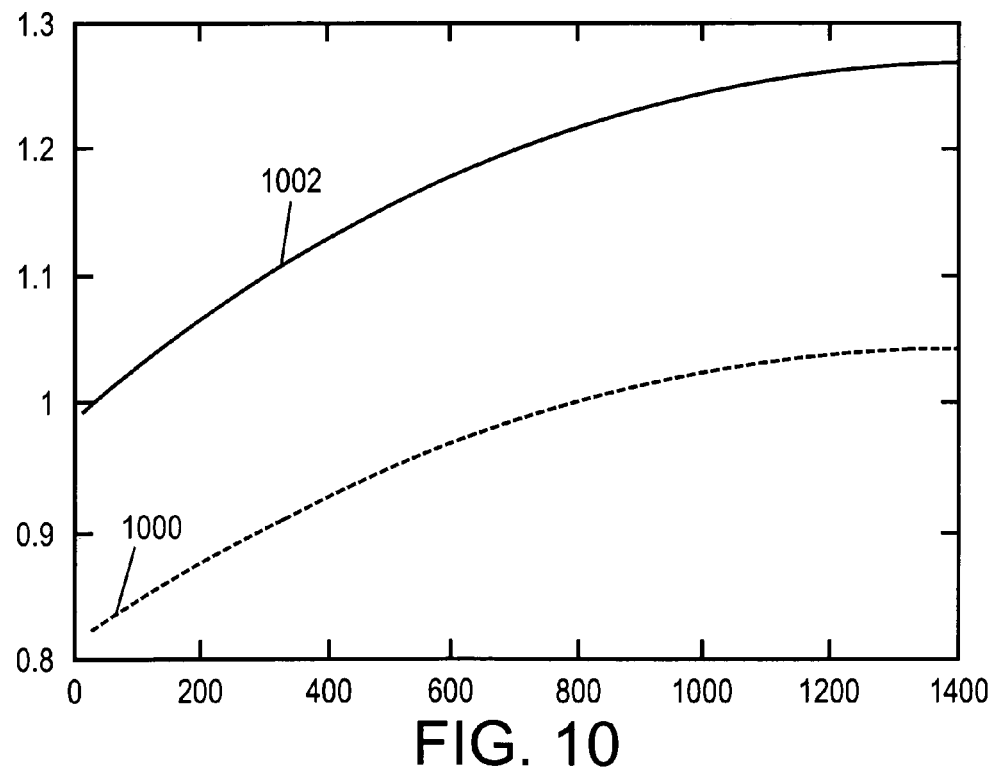
FIG. 10 is a diagram of temperature resistance curves at various temperatures, for an element comprised of approximately 2.5% aluminum, respectively normalized to 1.0 at 20° C. and to 1.044 at 1400° C.

The change in resistance induced by changes in the metallurgical content of the element alloy 102 can be represented and anticipated through the use of graphical temperature resistance curves as shown in FIGS. 9 and 10 and as discussed more thoroughly below. Briefly, FIG. 9 shows the graphical representation 900 of a temperature resistance curve of the heating element 101 measured across the "cold" to "hot" temperature range of approximately 20° C. to 1400° C. within a heating chamber or furnace, where the aluminum content of the element alloy is approximately 5.8% by weight. The graph line 900 represents the measured resistance of the heating element 101 as normalized to 1.0 at 20° C., with the relative resistance of the element rising to approximately 4.4% to 1.044 as the temperature environment for the element 101 rises to 1400° C. While 20° C. represents the approximate temperature at "room temperature," embodiments can also utilize other temperature scales, including those beginning with 0° C. The graphical representation 900 shown in FIG. 9 can be viewed as a reference baseline for the temperature-based resistance of the heating element 101 when the aluminum content of the alloy 102 is approximately 5.8%.

A physical consequence of the depletion of aluminum from the alloy core 102 to rebuild portions of the aluminum oxide protective layer 104 is an elongation of the heating element wire 101. The openings in the aluminum oxide layer 104 caused by the cracks 206 and fissures 208 in this layer 104 have the effect of spreading this layer 104. As these cracks 206 and fissures 208 heal with aluminum oxide during the heating step, the heating element wire 101 is lengthened. This elongation causes the electrical characteristics of the wire to change because any electrical current passing through the wire 101 has a greater distance through which to pass, such as between the opposing ends of the heating element wire 101. In particular, the resistance of the wire 101 is directly proportional to the length of the wire and therefore increases as the wire 101 elongates.

Yet another physical change to the heating element wire 101 from the depletion of aluminum from the alloy core 102 is the reduction of the cross-sectional diameter of the wire 101 as the alloy is consumed to fill cracks 206 and fissures 208 in the wire 101. The reduction in the cross sectional area increases the unit resistance of the heating element wire 101. This is because, for a given conductor of uniform material composition, such as the heating element wire 101, the electrical resistance of the conductor is inversely proportional to the cross-sectional area of the conductor. Thus, a small cross sectional area of wire has more resistance than a larger cross sectional area of wire that is made up of the same material. Therefore, as the depletion of aluminum from the alloy causes the cross-sectional area of the wire to decrease, the unit resistance of the heating element wire 101 increases.

Although the resistance of the alloy core 102 is reduced as the aluminum content of the core 102 is depleted, simply measuring the resistance of the alloy 102 at cold temperatures over time would not provide an accurate indicator as to the remaining content of aluminum within the core 102 and the corresponding condition of the element 101. This is because, during the aluminum depletion process, resistance in the wire 101 increases due to both the elongation of the wire 101 and the reduction in the cross-sectional area of the wire 101. Therefore, the net effect of the change in resistance at cold temperatures $R_c$ due to the depletion of aluminum content of the core 102 and the increase in resistance at any temperature due to the elongation and/or the reduction of the cross-sectional area of the wire 101 would be different than the effect of aluminum depletion when taken alone. However, in accordance with exemplary embodiments, the effects of aluminum depletion in decreasing the resistance of the core 102 at cold temperatures $R_c$ can be measured (both independent of and in conjunction with changes in resistance due to elongation effects) by comparing a baseline resistance or resistance ratio $X_R$ at some initial time $T_i$ and a subsequent measurement of the resistance or resistance ratio $X_R$ at some subsequent time $T_s$, after the initial composition of the core $C_i$ has changed to a subsequent composition $C_s$ having less aluminum.

Figure 2A:
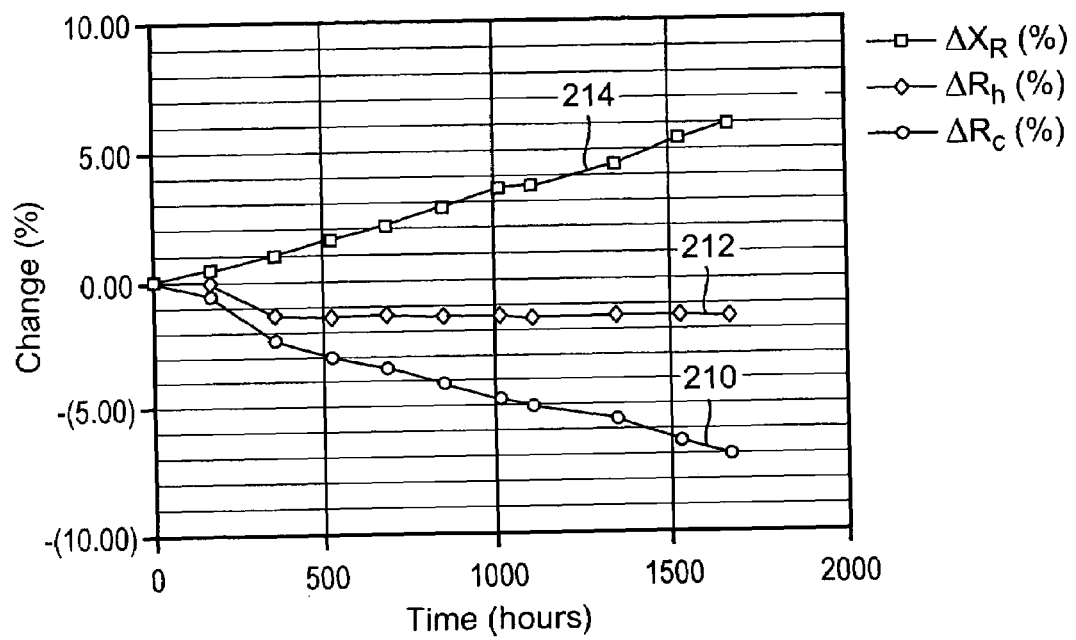
FIG. 2A is a graph of the percentage change of various resistance characteristics of a heating element over time.

FIG. 2A is a graph of the percentage of change of the cold resistance $R_c$ 210, the hot resistance $R_h$ 212 and the resistance ratio $X_R$ 214. The measurements of each of these values is taken over a period of time at discrete time intervals. From FIG. 2A, it is evident that the resistance ratio $X_R$ provides a good measure for indicating characteristics of a heating element over a period of time. Contrary to prior attempts, embodiments of the present invention monitor resistance values at frequent intervals. Such frequent monitoring ensures consistent values, and prevents statistical anomalies from clouding accurate measurements.

The heating element used in the tests shown in FIG. 2A is made up of the aforementioned preferred alloy composition having approximately 72.2% iron (Fe) 22.0% chromium (Cr), and 5.8% aluminum (Al). The diameter of the heating element used in these measurements is 8.0 mm. The hot temperature at which the hot resistance $R_h$ is measured is approximately 1000° C. in the measurements shown in FIG. 2A. It should be noted that the resistance ratio $X_R$ changes over a period of approximately 1700 hours from 0% to approximately 7%. The change approximates a linear response, and thus readily allows for extrapolation of data results for predicting ultimate failure of a heating element prior to the actual failure of the element. However, as will be discussed more thoroughly below, merely measuring the resistance ration, $X_R$, of the wire 101 at a particular time and/or temperature and comparing the reading to a reference baseline reading can be unreliable as an indicator of the condition of the material comprising the wire 101.

Because of the frequency with measurements are made (on average) every 150 hours in the example shown in FIG. 2A, the essentially linear change in the resistance ratio $X_R$ over time can be used reliably to extrapolate in predicting the overall lifetime of a heating element. This is useful, as prior techniques, which measured single resistance values and/or measured values less frequently than embodiments of the present invention, would produce unreliable results that could not be used for predicting ultimate failure of a heating element. However, estimating the slope of the line approximated by the resistance ratio $X_R$ data points, one can readily determine when the heating element has been used for approximately half of its useful life. Likewise, a prediction as to when the heating element has surpassed 90% of its useful life can be made, and thus new heating elements can be substituted prior to failure to maximize up time.

The process described in connection with FIG. 2 of depletion of aluminum from the core 102 to repair cracks 206 and fissures 208 in the aluminum oxide layer 104 continues repeatedly during each temperature cycle for the useful operational life of the heating element. This depletion continues until the aluminum level in the alloy 102 is depleted below a threshold level of the minimum amount of aluminum that can maintain the protective oxide coating layer 104 of the heating element wire 101. Generally, this minimum threshold level of aluminum within the core 102 is about 2.5% of aluminum content of the core 102. Reaching or surpassing the minimum threshold level of aluminum (i.e., the 2.5% aluminum content of the core) can cause various failure modes. For example, the iron in the alloy 102 having an insufficient aluminum oxide layer 104 can oxidize at a high rate and destroy the wire. Another failure mode can occur at higher temperatures when the iron portion of the alloy 102 simply melts and streams out of fissures in the aluminum oxide layer 104, such as the fissure 208 shown in FIG. 2.

Therefore, in light of the failure modes discussed above, the relative condition of the heating element during its useful life can be expressed in terms of the actual remaining aluminum content present in the alloy core 102 of the heating element wire 101. As discussed above, a typical aluminum content within the core 102 prior to any degradation associated with thermal cycling would be approximately 5.8% aluminum. After a period of time elapses and the stresses of multiple thermal cycles have been endured, the remaining aluminum content continues to be reduced until it reaches approximately 2.5%, which as discussed above indicates that the approximate failure point of the alloy core 102 has been reached. Those skilled in the art will appreciate that the actual percentages of alloy components monitored by the present invention can be varied according to specific desired outcomes and as product and/or safety specifications dictate.

In accordance with an embodiment of the present invention, the content percentage of remaining aluminum present in the alloy core 102 of the wire 101 can be determined by monitoring the changes in electrical characteristics that the wire undergoes as the aluminum content is depleted. That is, the level of aluminum remaining in the alloy can be expressed as a function of the resistance properties of the alloy. Thus, as described above, by measuring a change in the resistance ratio $X_R$ of the heating element wire 101 as the aluminum content changes, an accurate approximation of the remaining aluminum can be determined. From this approximation, a determination of how close the heating element wire 101 is to failure due to the loss aluminum in the alloy core 102 can be made. Additionally, other electrical characteristics can be monitored, some of which will be discussed below.

Embodiments of the present invention can measure relatively small changes in the resistance ratio $X_R$ to detect potential impending failures within a furnace making use of heating elements experiencing aluminum depletion. Therefore, because of the ability to detect changes in resistance characteristics of the heating element, potential non-uniform heating situations can be anticipated rather than reacted to. For example, in many furnaces, heating elements made up of multiple zones are used. Traditionally, a single temperature detection device, such as a thermocouple, might be used to detect the overall temperature of each heating element zone. Each of the heating element zones can be made up of multiple segments or circuits. These circuits can be connected in a parallel configuration. Therefore, if only a single circuit of a multi-circuit heating element zone becomes damaged and does not properly heat, the overall temperature of the heating element zone may not be lowered to an extent that could be detected by the single thermocouple. However, because of a single circuit of the heating element zone becoming inactive, the heat distribution of the heating element zone (and thus of the furnace) would be non-uniform, which could result in potential processing problems. On the other hand, by using the present invention, each of the multiple zones of each heating element could be monitored for changing resistance characteristics that might indicate failure or non-uniform heating within the zone. Thus, embodiments of the present invention measure properties over the entire zone for each zone to advantageously indicate a failure or impending failure, and to prevent such non-uniform heating situations within each zone (and thus within the furnace), thereby preventing losses in material, money, and operating time.

Figure 2B:
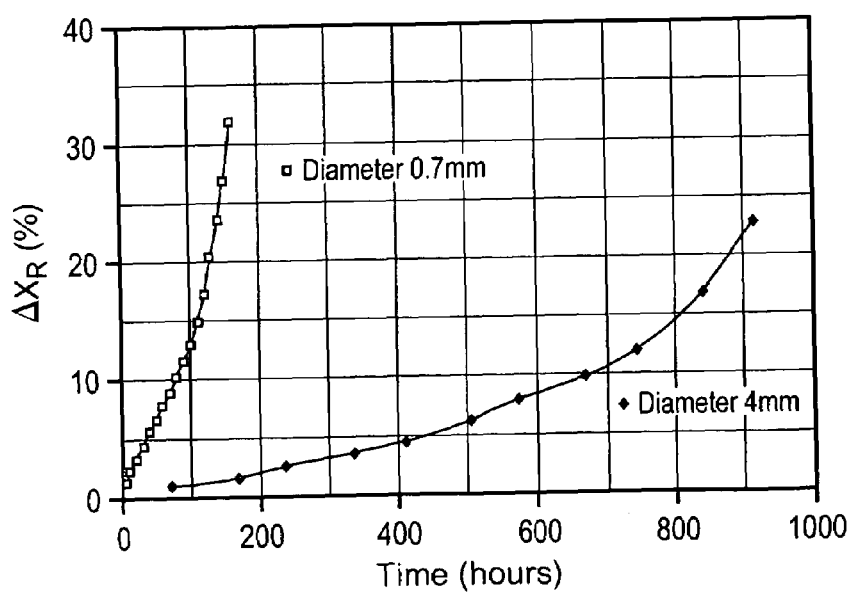
FIG. 2B is a graph of the percentage change of the resistance ratio $X_R$ for heating elements of different diameters.

In FIG. 2B, the percentage change of the resistance ratio $X_R$ is illustrated over time for two different wire thicknesses: 0.7 mm and 4 mm. The graph shown in FIG. 2B illustrates that both wires, although having different thicknesses, undergo similar changes over their lifetimes. Specifically, the overall change in the resistance ratio $X_R$ for both thicknesses of wire is within the 20–25% range. Therefore, this range of change in $X_R$ could be assumed to be a safe operating range for all wires having these diameters, or diameters between these diameters. It is advantageous to note that wires of varying thicknesses undergo similar changes over a lifetime, as both thick and thin wires have different advantages. For example, a large wire, while requiring a lower operating voltage, requires a higher current to produce the same power that could be produced by a thinner wire using a higher voltage and lower current. Thus, in conditions where only lower current amounts are available, one might be motivated to use a thinner wire at a higher voltage. Additionally, because of the lower physical mass and current requirements associated with lighter gauge wire, for economical reasons it may be desirable to use the thinnest wire possible that will yield acceptable results. FIG. 2B illustrates that the model used by the present invention to indicate the amount of aluminum depletion from the wire core is valid for such thin wires as well as for thick wires.

Figure 3A:
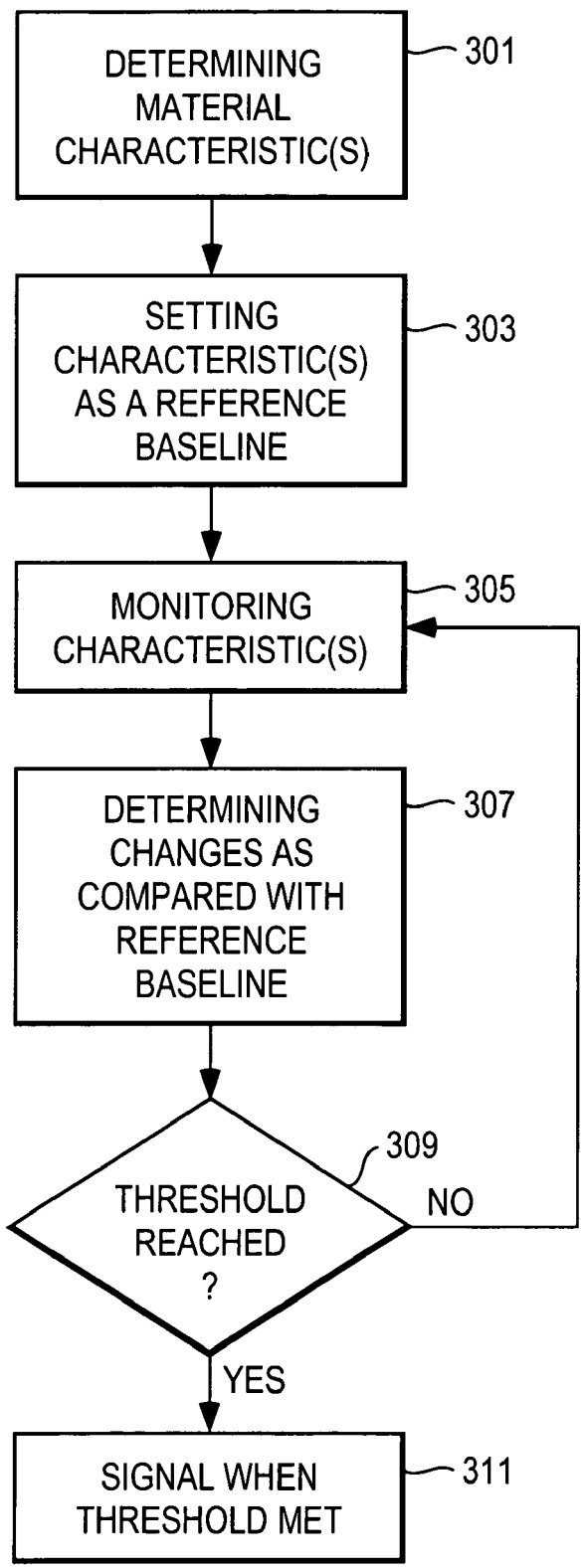
FIG. 3A is a flow chart illustrating an exemplary method associated with an embodiment of the present invention.

A method by which the characteristics associated with aluminum content of the alloy core 102 can be determined is shown in flow diagram form in FIG. 3A. In FIG. 3A, at least one characteristic of the material to be monitored is determined 301. Some characteristics of the material that can be monitored include, for example, physical attributes and measurements, electrical measurements and behaviors, and chemical compositions of alloy components. At least one characteristic of the initial composition $C_i$ of the material is measured at an initial time $T_i$ to establish a reference baseline 303. The measured characteristic(s) of material is then monitored in step 305 to determine any changes that can have occurred over time. Any such changes are then compared against the reference baseline in step 307, and a determination 309 is made regarding whether the change in the monitored characteristics has reached or exceeded a pre-determined threshold of change. If the threshold has not been reached or exceeded, the characteristics continue to be monitored in step 305. If, however, the threshold of change has been reached or exceeded, a signal is sent 311 to a decision making authority notifying that the level of changes has reached or exceeded the pre-determined threshold level.

Alternative embodiments of the invention provide for a reference baseline that is established across a range of time and/or temperature. The temperature resistance curve 900 of FIG. 9 can be viewed as a reference baseline measured across the temperature range of 20° C. to 1400° C. for a heating element wire 101 having an aluminum content of approximately 5.8%. Alternately, the x axis of FIG. 9 can also be expressed as a function of time as the temperature of the element increases from a relatively cold starting point. As has been mentioned above and will be discussed in more detail below, such a reference baseline measured across time and/or temperature can be more reliable, as a basis for comparison against changes in the composition and/or characteristics of the wire material that can be indicative of a pending failure of the material, than are single measurements made at particular time or temperature.

Figure 3B:
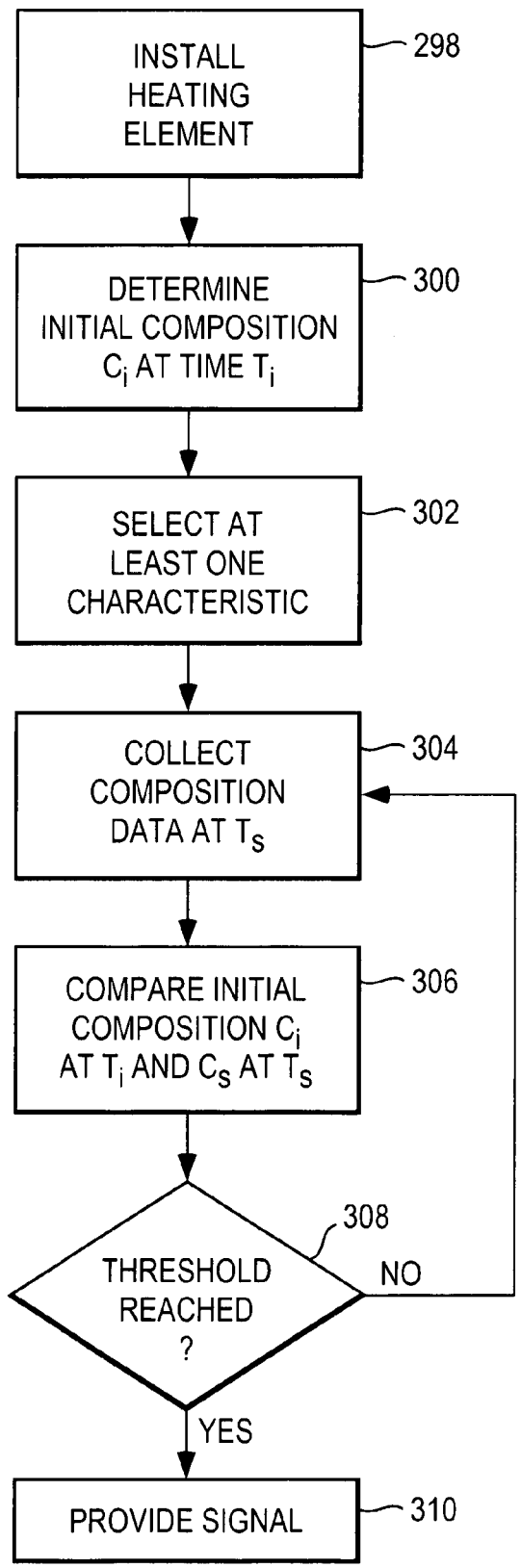
FIG. 3B is flow chart illustrating an exemplary method associated with an embodiment of the present invention.

Another exemplary embodiment of a method associated with the present invention is shown in flow diagram form in FIG. 3B. The embodiment shown in FIG. 3B monitors a particular characteristic of the material that is associated with the composition of the material. First, a heating element is installed at a physical location 298, such as in an oven used to heat up semiconductor wafers. In step 300 the initial composition $C_i$ of the material making up the heating element (e.g., aluminum) is determined in any suitable fashion at an initial time $T_i$. At least one characteristic associated with the initial composition $C_i$ is selected in step 302 at $T_i$ to be monitored (e.g., the electrical resistance of the material). This initial value for the characteristic is measured to establish an initial baseline condition relating to the composition of the material being monitored, against which subsequent measurements can be compared. In the exemplary embodiment, the percentage of aluminum content of the alloy 102 at $T_i$ is approximately 5.8%. Those skilled in the art will appreciate that different compositions, components, and percentages can be used without departing from the scope of the present invention.

Composition data is collected 304 at a later time $T_s$. The information collected at $T_s$ reflects the subsequent composition $C_S$ of the heating element 101 after a selected time period has elapsed since the initial time (i.e., after a period equal to $T_s-T_i$). The composition data reflecting the subsequent composition $C_s$ of the heating element wire at a subsequent time $T_s$ is compared to a predetermined threshold value (e.g., which can have been determined by way of calculation or experimentation, etc.) A determination 308 is made as to whether the threshold value has been met or exceeded (e.g., whether the aluminum content of the alloy has been depleted to a level of 2.5% of the alloy). If the determination 308 is negative, the composition data continues to be collected 304, where additional measurements are made for later values of $T_s$. However, if the determination 308 is positive, then a signal is provided 310 (e.g., an alarm is sounded) to notify the user that the threshold level has been reached (or exceeded).

In alternative embodiments of the present invention, the changes of composition within the alloy 102 can be determined by way of a variety of techniques. For example, as noted earlier, electrical resistance measurements are one technique of measuring the changes of composition within the heating element alloy 102. Thus, the change of a resistance value (e.g., the resistance ratio $X_R$) over time can be monitored and this information can be used to predict a pending failure. Specifically, as stated above, as the aluminum is depleted from the alloy 102, the resistance ratio $X_R$ increases steadily from an initial value of about 1.042 until it reaches approximately 1.250, which represents a failure state, or a state in which failure can be imminent.

Figure 3C:
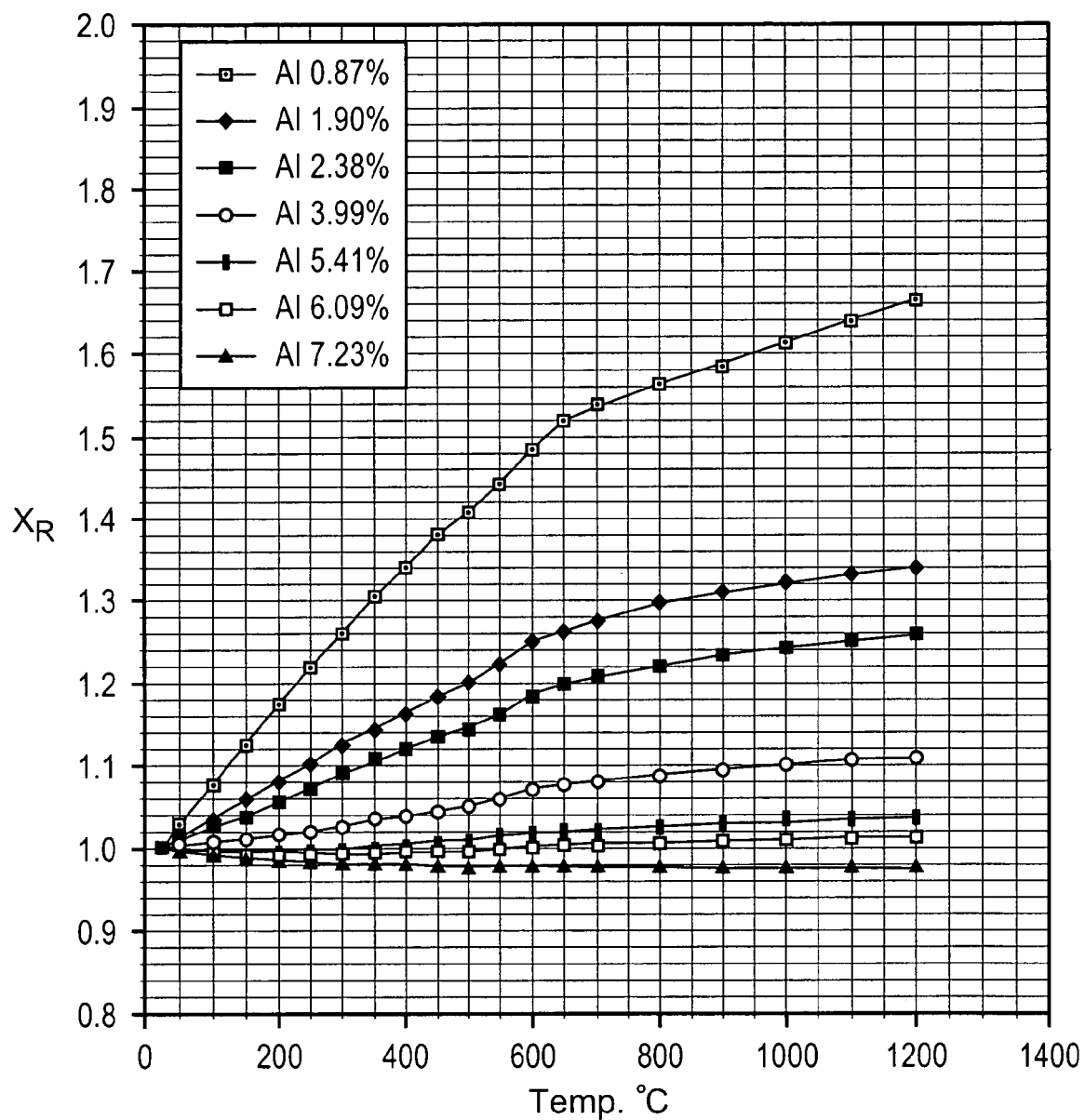
FIG. 3C is a graph of the resistance ratio $X_R$ at various temperatures, in a case where the alloy is cooled quickly.
Figure 3D:
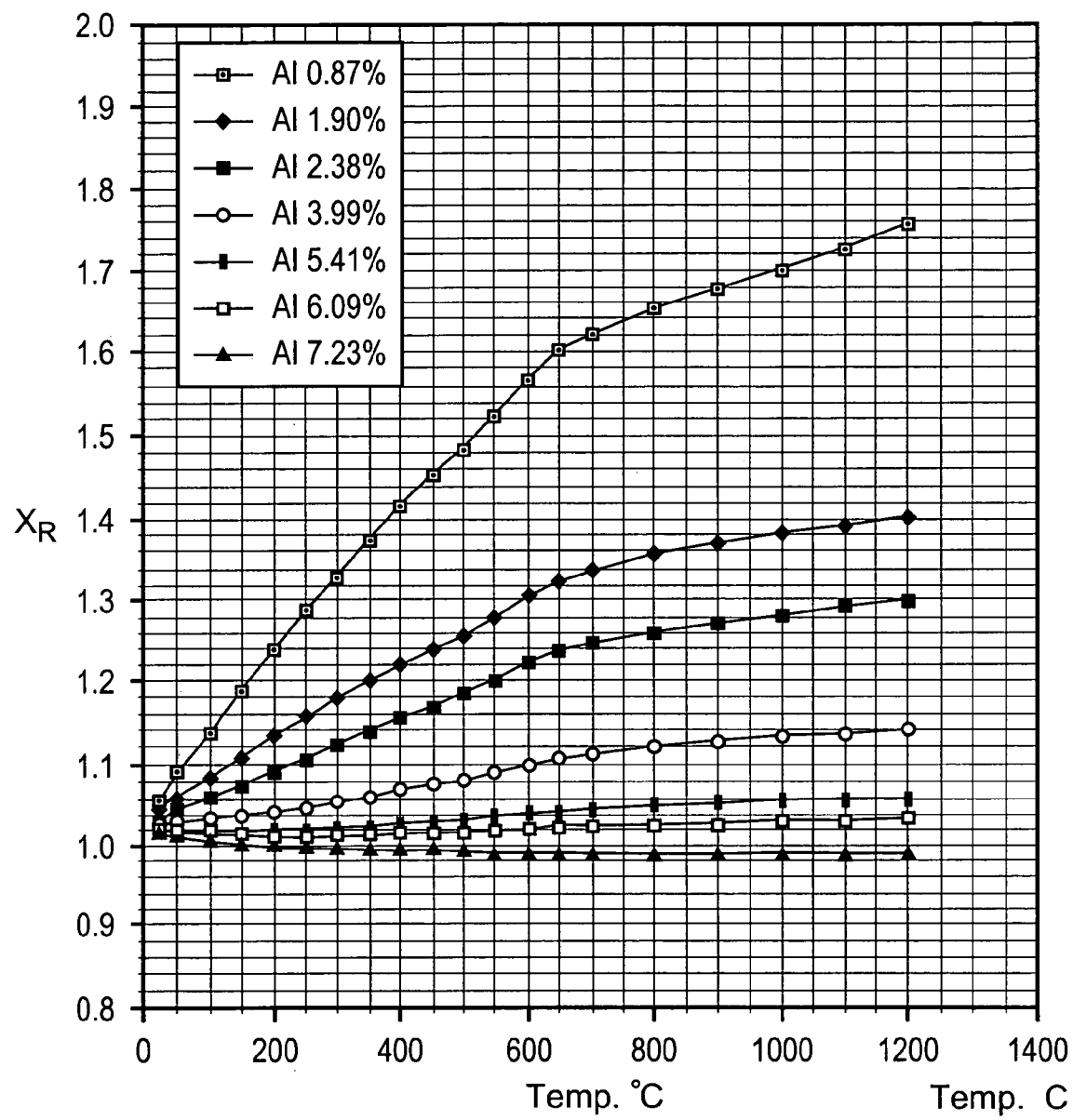
FIG. 3D is a graph of the resistance ratio $X_R$ at various temperatures, in a case where the alloy is cooled slowly.

FIGS. 3C and 3D show a heating element made up of a Fe/Cr/Al alloy wherein the percentage of chromium (Cr) is approximately 21%, and the percentages of aluminum (Al) and iron (Fe) are varied. Several results for differing percentages of aluminum content of the alloy are shown in the graph, beginning with the lowest percentage (0.87%) of aluminum content and ending with the highest percentage (7.23%) of aluminum content. The percentage content of iron (Fe) is varied to make up the remaining portion of the alloy composition of the heating element. These Figures show the expected resistance ratio values $X_R$ for various percentages of aluminum content. In FIG. 3C the temperature of the heating element is cooled quickly between measurements of hot resistance $R_h$ and cold resistance $R_c$, while in FIG. 3D the temperature is cooled more slowly at a controlled pace between these measurements.

Subtle shifts in measured resistance values can be observed between processes that allow the element to be cooled quickly, such as in FIG. 3C, and processes that allow the element to be cooled more slowly, such as in FIG. 3D. However, in both cases, the change in the resistance ratio $X_R$ for the aluminum content range associated with an embodiment of the present invention (i.e., with maximum and minimum percentages of aluminum content of 5.8% and 2.5%, respectively) is about 20–25%. This value is obtained by observing the graphed values closest to the maximum and minimum aluminum content percentages (i.e., the graphed values of 6.09% and 2.38%, respectively). Additionally, in both cases shown in FIGS. 3C and 3D, the measurements are taken at frequent time intervals to provide maximum accuracy in measurement. In FIGS. 3C and 3D, the heating element having the lowest composition of aluminum (0.87%) has the largest value of the resistance ratio $X_R$.

Figure 3E:
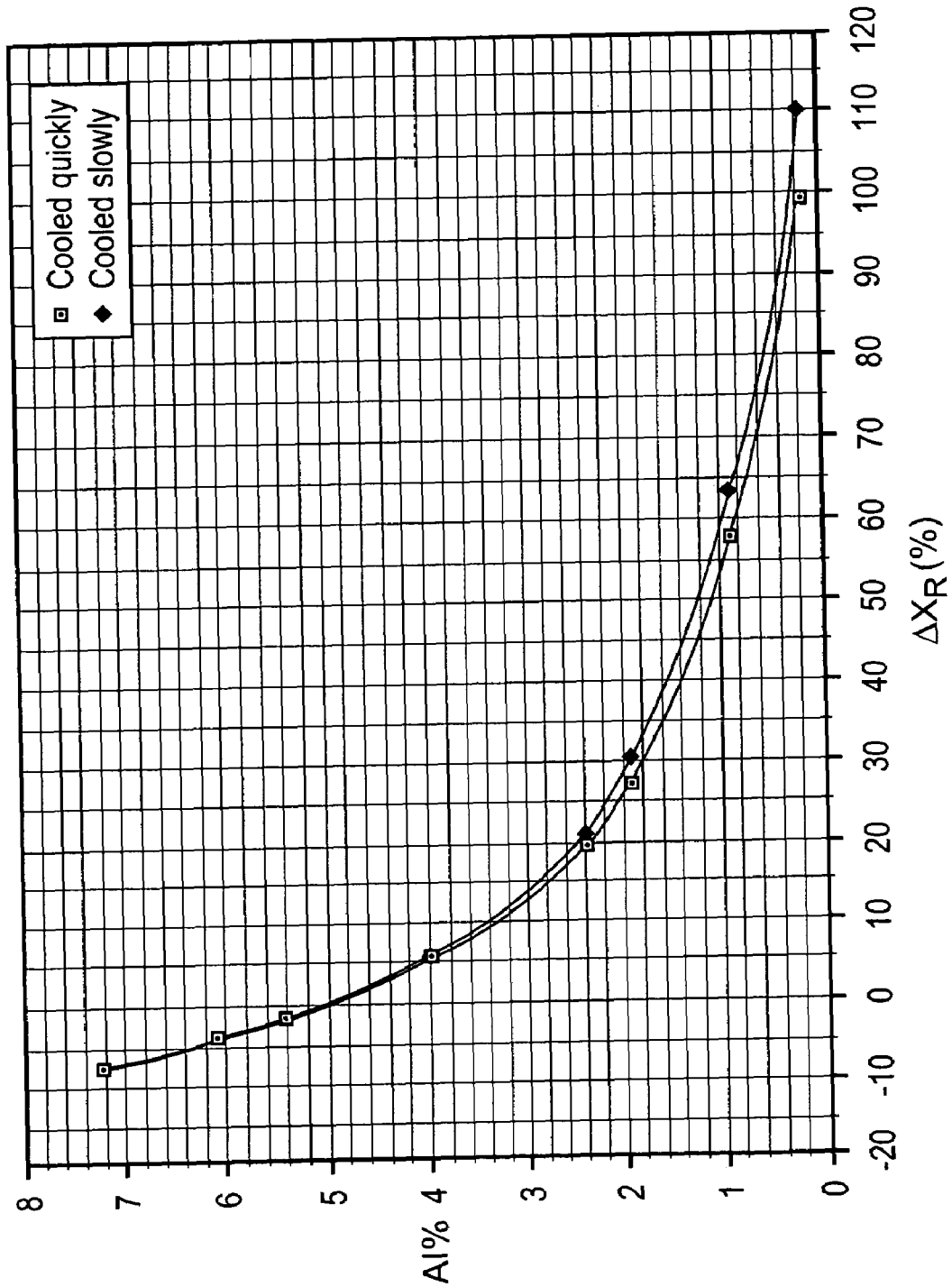
FIG. 3E is a graph comparing the percentage change of the resistance ratio $X_R$ of alloys having different aluminum content percentages when cooled quickly versus when cooled slowly.

The graph in FIG. 3E represents a comparison between the data shown in FIG. 3C with the data shown in FIG. 3D. Thus, the graph shown in FIG. 3E illustrates the percentage of change of the resistance ratio $X_R$ with respect to the aluminum percent content of the alloy for both quick-cooled and slow-cooled elements. The graph shown in FIG. 3E illustrates that whether an alloy is cooled quickly or cooled slowly, the results are similar. Specifically, in FIG. 3E it is shown that both the quickly cooled alloy and the slowly cooled alloy experience a change in the resistance ratio $X_R$ of about 20–25%, which falls within the expectations of the model for aluminum depletion in accordance with embodiments of the present invention.

According to an embodiment of the present invention, information collected by way of the present invention can be represented in a relational data table, such as the relational data table shown in FIG. 4, for example. Specifically, information collected and stored in the relational data table of FIG. 4 can be sampled at multiple, discrete times, which can be separated according to a pre-determined time interval. The specific times at which measurements are taken $T_1$–$T_n$ are shown in column 400 of the relational data table. Corresponding hot resistance values $R_{h1}$–$R_{hn}$ and cold resistance values $R_{c1}$–$R_{cn}$, taken at each time shown in column 400, are shown in columns 402 and 404. The corresponding resistance ratio values $X_{R1}$–$X_{Rn}$ are stored in column 406 of the data table. Additionally, the relational data table can contain information regarding the amount of the remaining alloy $A_{R1}$–$A_{Rn}$, which can be stored in an additional column such as column 408 of the relational data table shown in FIG. 4. This amount can be calculated, as indicated above, by a pre-determined formula using a variable such as the resistance ratio value shown in column 406. Additionally, it will be appreciated by those skilled in the art that multiple variables other than the variables shown in the exemplary table of FIG. 4 can be used in determining the percentage of alloy component remaining. Therefore, the relational data table shown in FIG. 4 could be changed to incorporate any values desired to be monitored that could be used in determining the amount of alloy component remaining (e.g., voltage or current measurements, measurements made by an active, embedded sensor, etc.).

The resistance characteristic values being measured in columns 402, 404, and 406 of the relational data table shown in FIG. 4 can change in a variety of manners. For instance, the resistance values can change gradually, indicating a natural aging process of the heating element. The resistance values can experience a rapid change, which can indicate a localized failure point, such as a contaminated area. Therefore, the changes in values being measured within the relational data table can indicate more than one failure mode of the heating element being monitored.

The exemplary alloy described above for use as a heating element (i.e., an alloy containing 72.2% iron, 22.0% chromium, and 5.8% aluminum) has a positive temperature coefficient of resistance. This means that the value of resistance measured in the alloy increases as the temperature of the alloy increases. Thus, if the resistance of a sample of wire alloy is measured at about 20° C., or ambient conditions, and then the resistance of the same sample is measured at a higher temperature, the value of the resistance will be greater at the higher temperature. One example occurs when a sample of wire is heated from about 20° C. to about 1300° C. In this instance, the sample wire alloy will experience an increase in resistance of about 4.2% at the higher temperature over the resistance present at the ambient temperature. This can be expressed as a resistance ratio $X_R$, as defined in Equation 1, which in this case would yield 1.042. As aluminum is depleted from the alloy, and the wire alloy reaches the end of its useful life (e.g., having about 2.5% aluminum content remaining), the increase in resistance over the same range is found to be about 25%, or the resistance ratio $X_R$ is about 1.250.

As explained above, the nature of the change in the alloy's resistance characteristics are such that the resistance at the hot temperature $R_h$ remains relatively constant, while the resistance at cold temperatures $R_c$ decreases as the aluminum content is depleted from the alloy. Those skilled in the art will appreciate that the change in the composition of the alloy is generally small and happens gradually over long periods of time. Thus, the resistance ratio $X_R$ must be accurately monitored over long periods of time. For example, useful lifetimes of 2–8 years are not uncommon in such wire alloy heating elements. Those skilled in the art will appreciate that in addition to accurately monitoring resistance characteristics of the alloy (e.g., the resistance ratio $X_R$) data regarding the characteristics of the alloy can be extrapolated to predict future conditions of the alloy. For example, integration techniques can be used to predict the remaining useful life of such a heating element.

Referring now to FIGS. 9–14, there are shown a series of temperature resistance curves for heating element materials measured across an exemplary temperature range, e.g., 20° to 1400° C., wherein one or more physical and/or metallurgical changes in an element can be monitored to anticipate when an element is approaching failure. The resistance curves can be graphed from resistance measurements or readings taken while passing an electrical current through the element 101. In exemplary embodiments, the current can be directed through one or more elements without removing the elements from their environment, such as a heating chamber or a furnace. In such a manner, the elements do not need to be taken out of service; nor does the furnace need to be taken out of operation or shut down; and, in fact, measurements can be taken while the elements are in actual heating operation. While measurements of electrical resistance will be discussed below in conjunction with exemplary embodiments, other aforementioned characteristics such as current, voltage, or temperature could be measured as a reference baseline without detracting from the features of exemplary embodiments.

FIG. 9 shows a baseline resistance curve 900, normalized at its beginning to 1.0, measured across a temperature range of 20° C. to 1400° C. for an element or material with an aluminum content of approximately 5.8% by weight. The curve 900 constitutes a first graphical representation of the resistance of the material. This particular alloy is utilized as an example and not a limitation because it is representative of the composition of heating element wires used in furnaces to heat microchip components. Embodiments are by no means limited to this particular alloy composition, and any number of alternate alloys can be used with exemplary embodiments to monitor the condition of a conductive material. The normalized resistance of the alloy shown in FIG. 9 rises to approximately 1.044 at 1400° C., representing an increase in resistance in the element of approximately 4.4% across the exemplary temperature range.

Referring to FIG. 10, there are shown temperature resistance curves 1000 and 1002 graphed across the same temperature range for the alloy 102 as shown in FIG. 9, but graphed after the aluminum content of the alloy has been depleted through metallurgical degradation to approximately 2.5%. For comparison purposes, the resistance curve 1000 of FIG. 10 has been normalized to the graph of FIG. 9 at a temperature of 1400° C., where the relative resistance is approximately 1.044. The resistance curves 1000 and 1002 constitute second graphical representations of the resistance characteristic of the material. As can be seen from FIG. 10, the resistance for the metallurgically-degraded element 101 is lower at cold temperature, approximating 0.822 in the exemplary embodiment demonstrated by resistance curve 1000. In particular, the electrical resistance is lower at room temperature for the 2.5% aluminum alloy than for the 5.8% aluminum alloy. Thus, by measuring and graphing the resistance of the alloy 102 across a temperature range, one can compare whether the aluminum content of the alloy has changed from a prior reference baseline measurement.

Curve 1002 shows the graphical representation of the temperature-based resistance for the depleted aluminum alloy as normalized at 20° C. to 1.0. The relative resistance at 1400° C. for resistance curve 1002 is approximately 1.27, showing a change in the resistance characteristic of the element of an increase of approximately 27% from cold to hot temperature, which is significantly higher than the alloy comprised of 5.8% aluminum. The normalized resistance curve 1000 also shows an approximate 27% increase in resistance over the 20° C. to 1400° C. range. In contrast, as shown in FIG. 9, the resistance of the non-depleted element increases only approximately 4.4% from a cold to a hot temperature.

A geometric comparison between the baseline graph of FIG. 9 and a selected resistance curve of FIG. 10 can determine whether the geometric differences exceed a predetermined threshold, thereby signaling the deterioration and/or pending failure of the element. The resistance measurements taken to produce the non-baseline resistance curves (i.e., curves 1000 and 1002) were taken after a significant number of heating and cooling cycles and close to the expected failure of the element, as initially established by measurement trial and error. Use of these measurements can establish a predetermined threshold level or value for the geometric difference between the baseline curve 900 and the resistance curves 1000 or 1002 for a used element that is approaching failure or has exceeded its useful or reliable life. By comparing the geometric difference between the reference baseline and the resistance curve of an operating element, a determination can be made whether the difference exceeds the predetermined value, thereby indicating the element is about to fail or has reached the end of its expected useful life. If such an indication is made, a signal can be initiated to alert the need to replace the element. The geometric comparison can be a graphical comparison, an algorithmic comparison, a mathematical analysis, or any combination thereof; the embodiments are not so limited.

Figure 11:
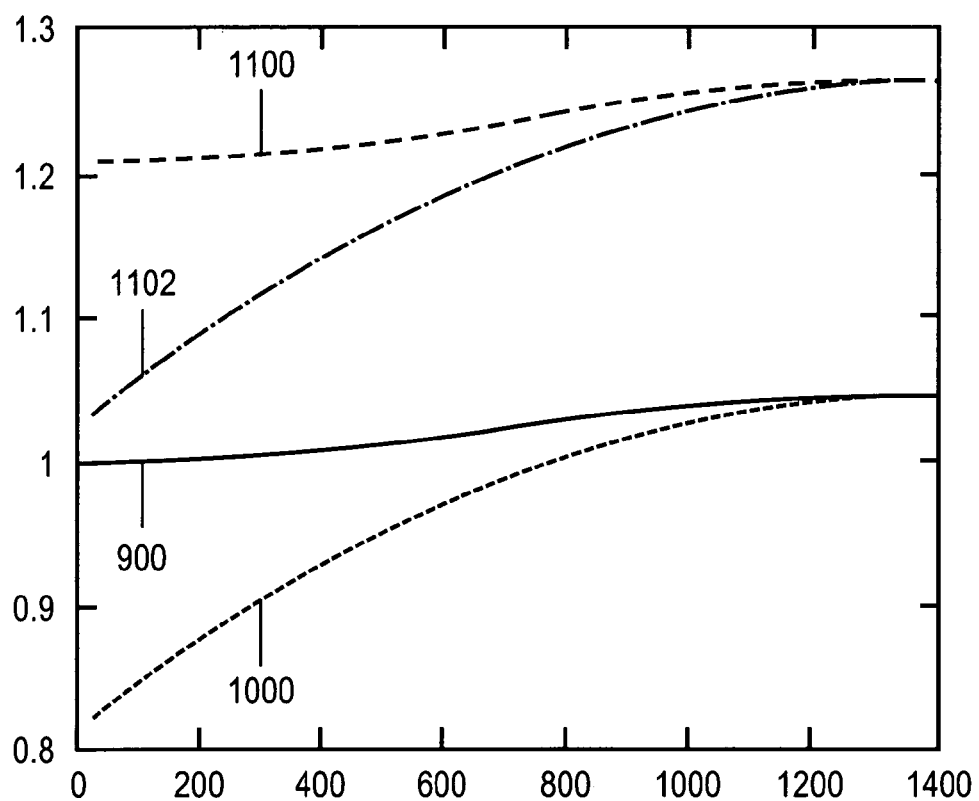
FIG. 11 is a diagram showing temperature resistance curves across a temperature range, for elements comprised of different alloy compositions and of different lengths.
Figure 12:
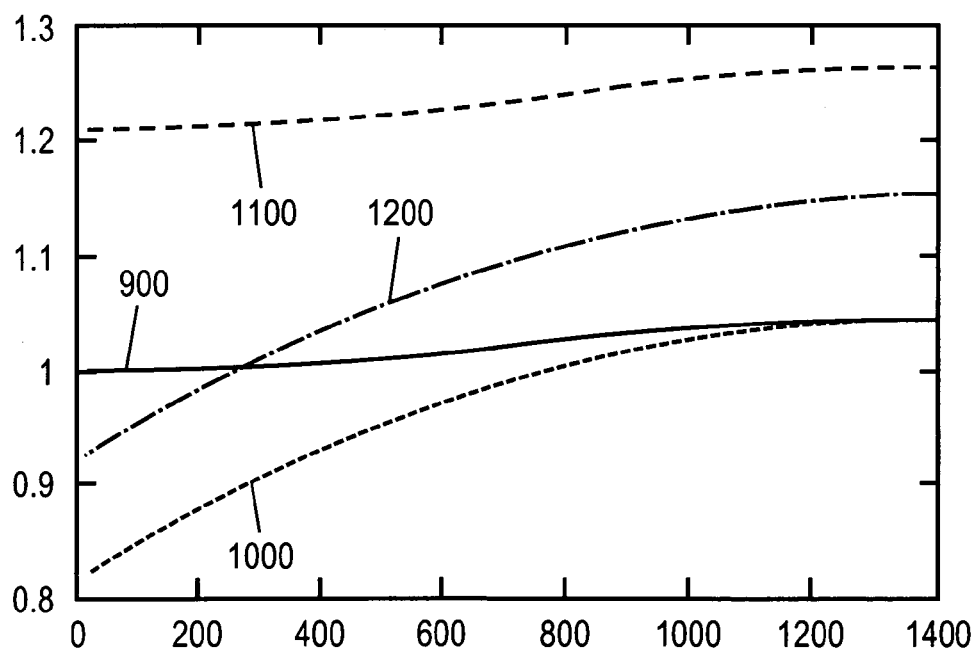
FIG. 12 is a diagram showing temperature resistance curves across a temperature range, for elements comprised of different alloy compositions and of different lengths and where the effect of composition and elongation are measured disproportionately.
Figure 13:
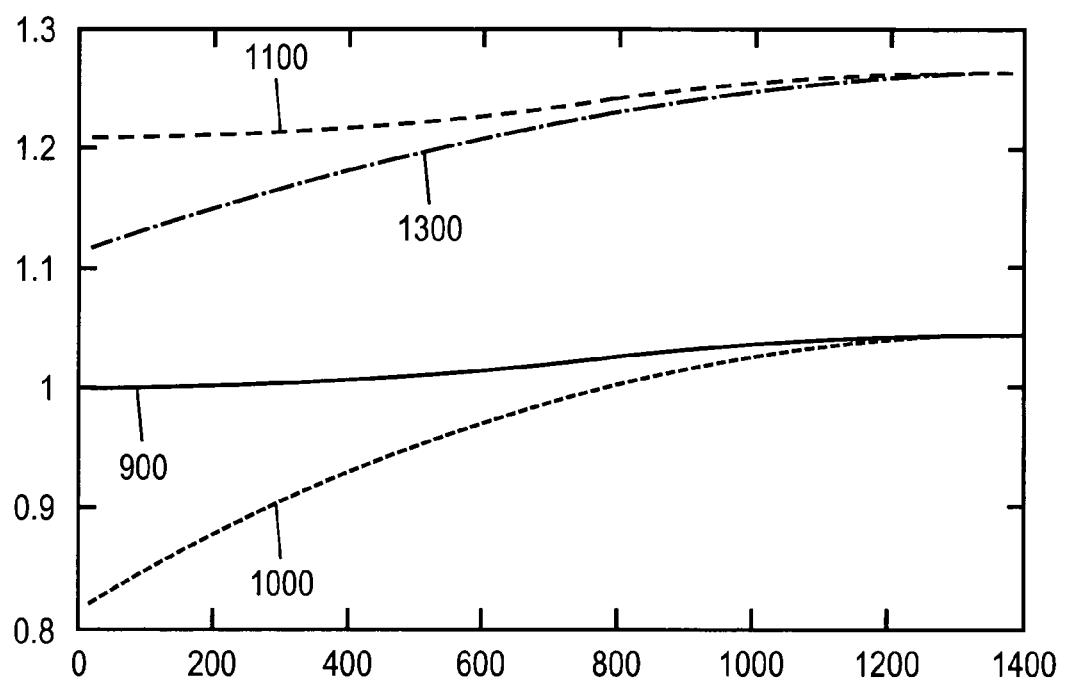
FIG. 13 is a diagram showing temperature resistance curves across a temperature range, for elements comprised of different alloy compositions and of different lengths and where the effect of composition and elongation are measured disproportionately.

Referring now to FIGS. 11–13, there are shown temperature resistance graphs for heating elements that have undergone various degrees of change attributable to metallurgical degradation and/or elongation during the heating and cooling cycles sustained in a heating chamber or furnace. Curve 900 and curve 1000 in each of these Figures represents the same baseline curve shown in FIG. 9 and the depleted aluminum curve shown in FIG. 10, respectively. Referring first to FIG. 11, curve 1100 shows the resistance curve measured across the temperature range of 20° C. to 1400° C. for an element that has expanded linearly, or elongated, because of the stresses and cracks imposed on the element during the heating and cooling cycles as discussed above. The elongation curve 1100 has been normalized to a relative resistance of 1.27 at 1400° C. to provide a comparison with the resistance curve 1002 for an element whose metallurgical content has degraded. As can be seen from FIG. 11, the exemplary elongation resistance curve 1100 shows an approximate 26% increased resistance from the baseline resistance shown by curve 900, with a similar lateral resistance increase of approximately 6% from a cold to a hot condition.

Curve 1102 represents a combination resistance curve for an element that has suffered the combined effects of metallurgical degradation of aluminum to approximately 2.5% and of elongation. Curve 1102 has also been normalized to 1.27 at 1400° C. and represents a condition where the effects of metallurgical degradation and elongation are approximately equal. In contrast, FIGS. 12 and 13 present conditions where the different strains, degradations, and changes to the elements have not been applied to the material in equal proportions. Curve 1200 of FIG. 12 represents the resistance curve of an element wherein the resistance change attributable to metallurgical degradation is approximately twice the change attributable to the elongation of the element. As expected, the resultant curve 1200 more closely approximates the purely metallurgical change curve 1000. Curve 1300 of FIG. 13 represents the resistance curve of an element where the resistance change of the element from of elongation is approximately twice the metallurgical degradation of the element.

Referring back to FIG. 12, there can be seen an intersection of the reference baseline curve 900 with the combination resistance curve 1200 at approximately 275° C. This example demonstrates that merely taking a resistance measurement of a used element at 275° C. could produce a resistance reading closely matching the baseline value for that temperature, falsely indicating an element in good condition. Embodiments of the present invention can accommodate for such differences by measuring one or more characteristics of the element 101 across time and/or temperature and geometrically comparing the measurements against a reference baseline to determine whether the condition of the element 101 is approaching a point of failure. By establishing a plurality of geometric models, exemplary embodiments can test for any combination of metallurgical, elongation, and cross-sectional changes in a heating element, while the element remains in a furnace, for threshold conditions indicative of pending failure and/or end of useful life.

Figure 14:
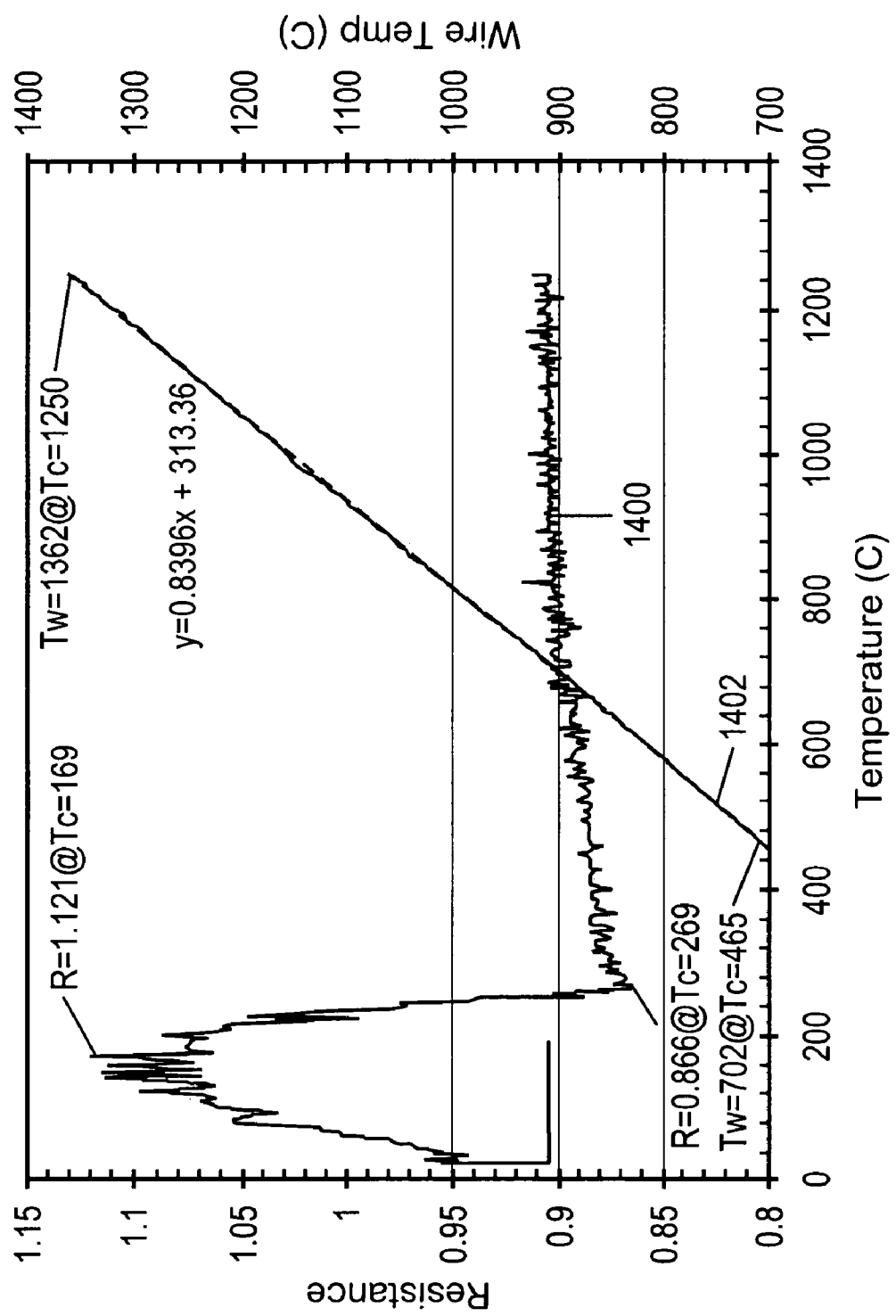
FIG. 14 is a diagram showing the detailed resistance changes of a degraded element as the element is heated across a temperature range.

Referring now to FIG. 14, there is shown a detailed resistance curve 1400 that demonstrates another physical phenomenon associated with the degradation and/or failure of heating elements 101 in a furnace. The resistance of the exemplary element 101, which is known in this example to have undergone approximately 2,000 heating/cooling cycles, at a cold temperature is approximately a normalized value of 0.905. During the first 270° C. of warmup, the resistance of the element 101 spikes to approximately 1.121 before falling and leveling out around 0.90. This sudden change in normalized resistance is caused by the initial application of power, causing heating of the material at the cracks in the element, and in turn expanding the gaps in the material temporarily. For example, cracks in the material are opening and/or former welded cracks are breaking. Once the element 101 heats sufficiently (in this case the wire temperature reaches about 400° C.), it expands and pushes the material back together; and the resistance readings 1400 return to normal. These measurements indicate that the furnace does not need to operate at its full range of power or duration of time to effect the impact of the cracking and expanding of the element 101, which is shown in the exemplary graph of FIG. 14 to have occurred in the first 400° C. of operation. The x axis of the graph represents the temperature of the heating chamber, and the right side axis represents the temperature of the wire itself as it heats up. The heat slope of the wire is provided by the formula y=0.8396x+313.36 to show the relative temperature of the wire as the temperature (x) of the chamber increases.

Because many of the resistance measurements yield relatively low values, accurate measuring mechanisms must be employed to properly measure and monitor this information. For example, a typical resistance value of a given temperature zone found in a heating elements of a high temperature furnace is on the order of 0.250 to 2.000 ohms. This means that, in accordance with a preferred embodiment of the present invention, in order to detect an immanent failure in a heating element having an original value of 0.250 ohm, the measuring device must accurately detect a 20% change in cold resistance, or about 0.05 ohm. Achieving these levels of measurement accurately normally requires the heating element to be disconnected from the power source. The power source is disconnected to ensure that the neither power supply nor any of the components influence the accuracy of the readings. However, other embodiments of the present invention can be used to measure resistance values with power connected, for example by way of current and voltage measurements, and do not depart from the spirit of the present invention.

Figure 5:
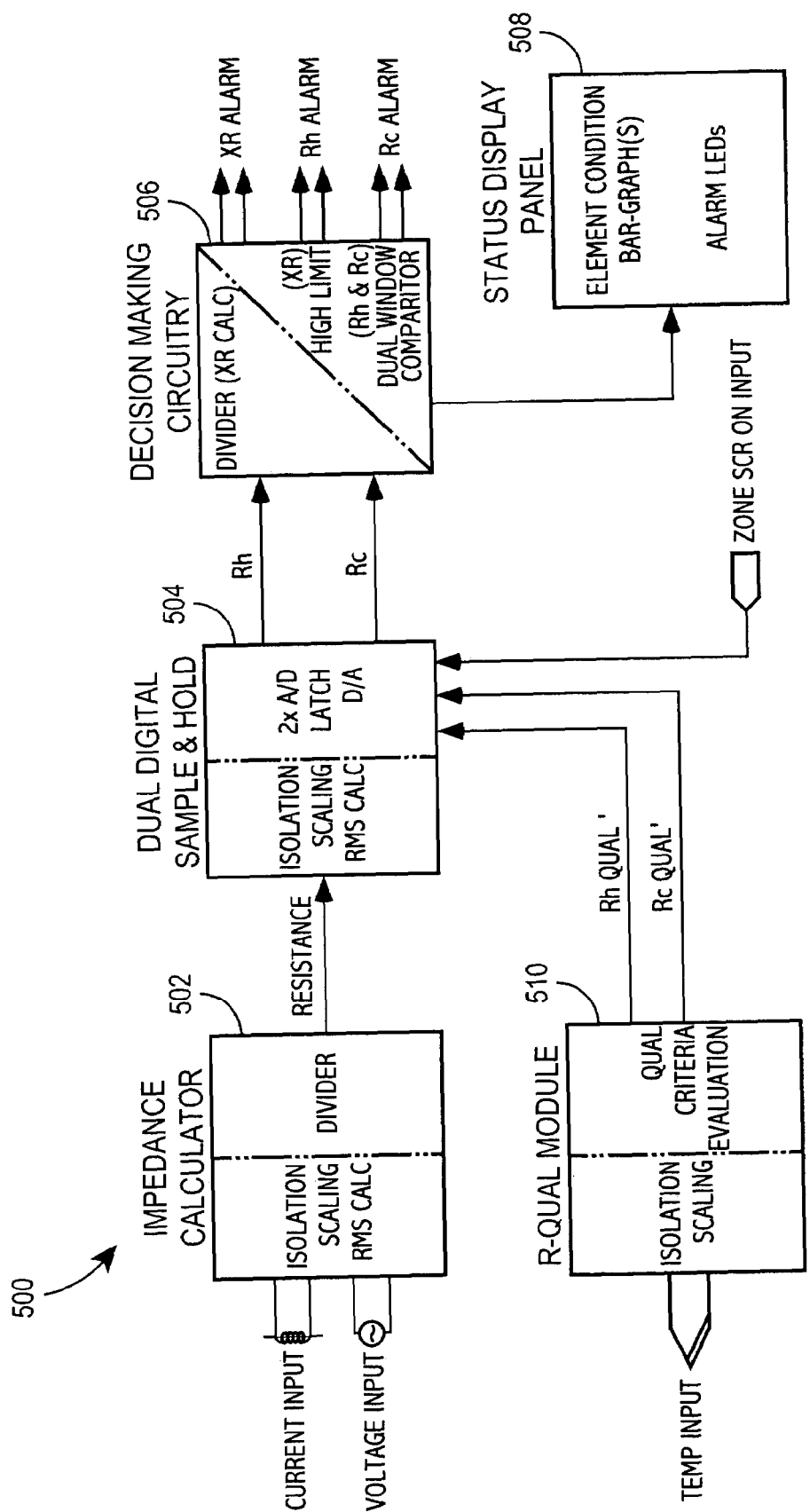
FIG. 5 is a block diagram of an impedance monitor in accordance with an embodiment of the present invention.

FIGS. 5–8C show exemplary apparatus and means for performing the various and specific functions for monitoring the condition of a material and initiating an alarm signal should exemplary embodiments determine that a change in the condition of the material reach or exceed a predetermined threshold value. Referring to FIG. 5, there is shown an impedance monitor 500, which can be used for monitoring changes in impedance or resistance, at the levels of accuracy necessary for detecting changes in alloy composition, is shown in block diagram form. The impedance monitor 500 is made up of three main components: an impedance calculator 502, sample and hold circuitry 504, and decision making circuitry 506. Additionally, a display panel 508 and a quality module 510 can also be optionally used by the impedance monitor 500. The display panel 508 is used for displaying status other information. The R-Qual module 510 provides signals regarding the quality of the $R_h$ and $R_c$ measurements. The signals from the R-Qual module 510 indicate that measurements of $R_h$ and $R_c$ can be sampled, as they will produce valid measurements. It will be recognized by those skilled in the art, that although the term resistance has been used throughout this application, impedance, which takes into account reactive elements can also be measured, can also be useful in determining the percentage of an alloy component within an alloy. Thus, the impedance monitor 500 is entitled in FIG. 5 with respect to the more generic term impedance.

Exemplary schematics for each of the main components of the impedance monitor 500 are shown in FIGS. 6, 7, 8A, 8B, and 8C. The schematics of these figures show an exemplary embodiment of the present invention that uses pure resistance measurements (i.e., without any reactive impedance components); however, as mentioned above, those skilled in the art will recognize that each of the exemplary schematics could readily be modified to take into account measurements of reactive impedance components. Within each of these schematic diagrams, values are shown for voltage, current, resistance, capacitance, and so forth. Additionally, where possible, standard part numbers are indicated, such that one of ordinary skill would be able to readily obtain the parts to make and use the invention. However, those skilled in the art will recognize that values and parts shown in the figures can be changed somewhat without departing from the spirit of the present invention. Additionally, it will be understood by those skilled in the art that some additional power circuitry can be required to provide power to the impedance monitor 500 and the various circuits shown in the schematic diagrams of FIGS. 6, 7, 8A, 8B, and 8C.

Figure 6:
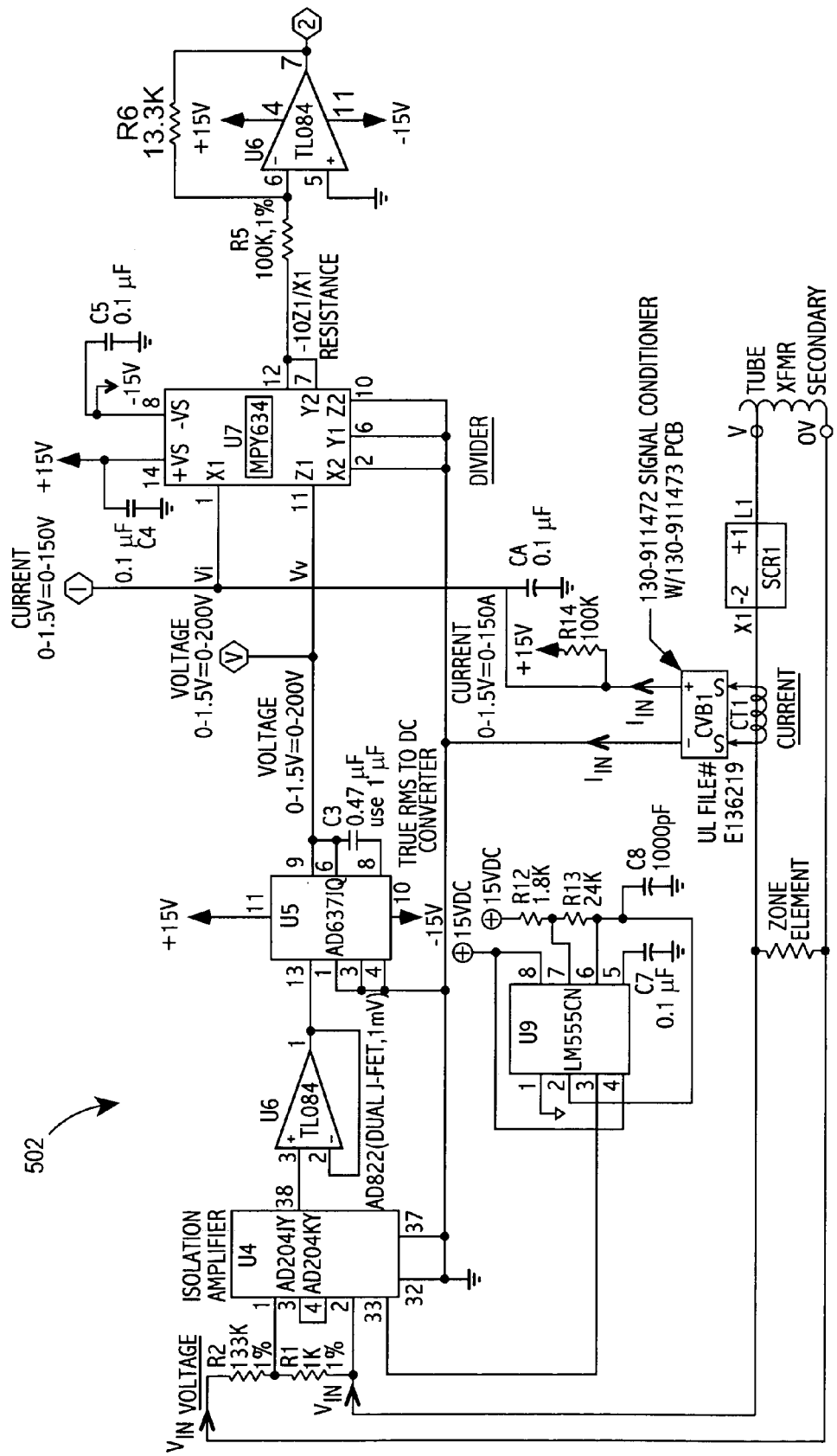
FIG. 6 is a schematic diagram of an impedance calculator in accordance with an embodiment of the present invention.

In FIG. 6, the impedance calculator 502 of the impedance monitor 500 is shown in the form of a schematic diagram. The impedance calculator 502 uses isolation scaling and RMS calculations to determine impedance. Specifically, the impedance calculator 502 measures the voltage and the current, by way of induction, of the heating element desired to be analyzed, and is able to determine the heating element's resistance from these measurements. Specifically, the "TUBE XFMR SECONDARY" represents the external heating element system to be measured by the impedance calculator 502. The current produced by way of the transformer coupled to the heating element load is rectified by way a silicon control rectifier (SCR), and the applied voltage is represented as $V_{in}$. The current is measured by way of the signal conditioner, and output at Node I, while the output voltage is supplied as an output at Node V, and the divider produces a signal proportionate to the resistance of the heating element load, which is calculated from the voltage and current measured. This information is then output by way of the Node 2 to the sample and hold circuitry 504 shown in FIG. 7, which is connected to the impedance calculator by way of Node 2, also shown in that figure.

Figure 7A:
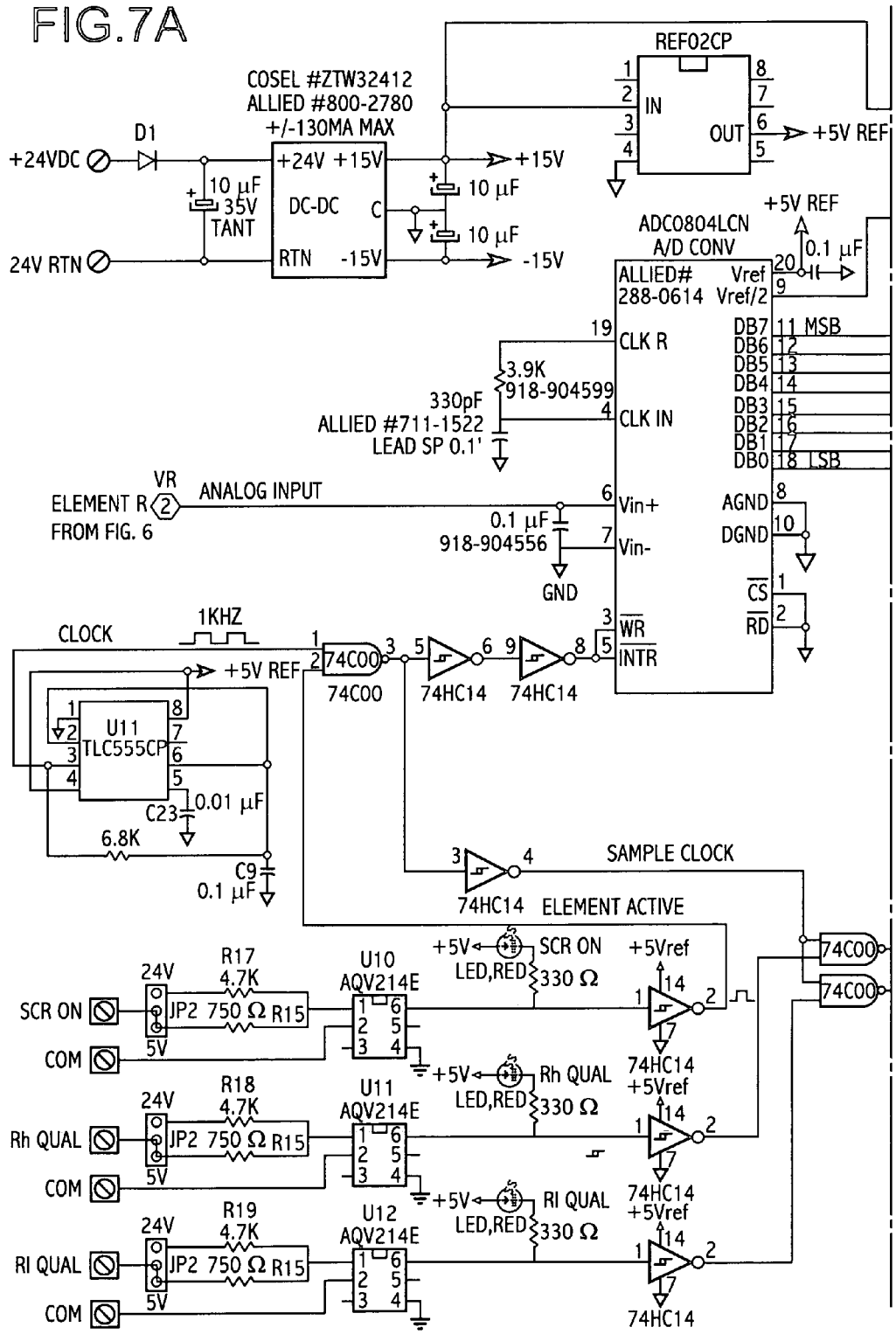
FIG. 7, consisting of FIGS. 7A and 7B, is a schematic diagram of digital sample and hold circuitry in accordance with an embodiment of the present invention.
Figure 7B:
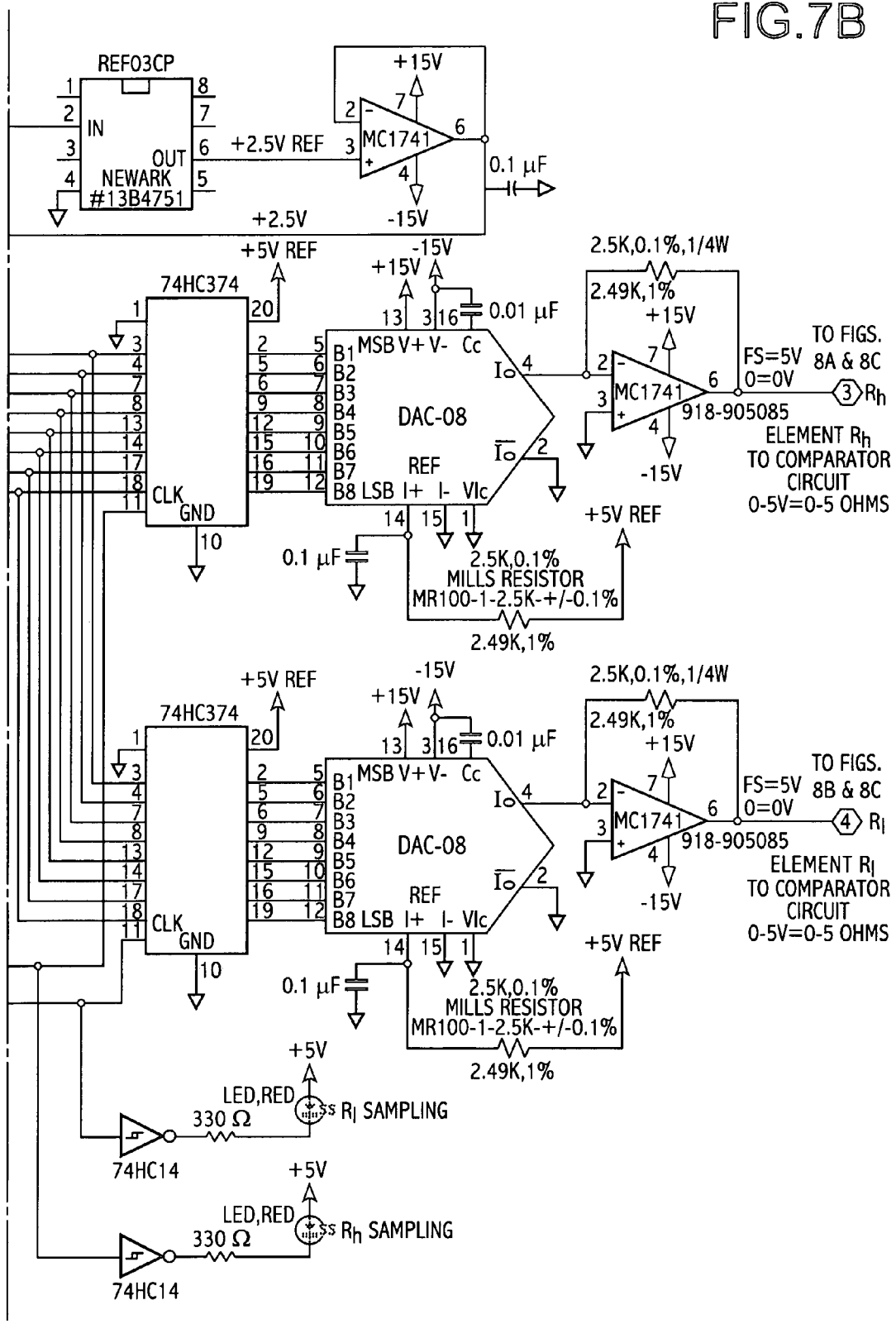
Figure 8A:
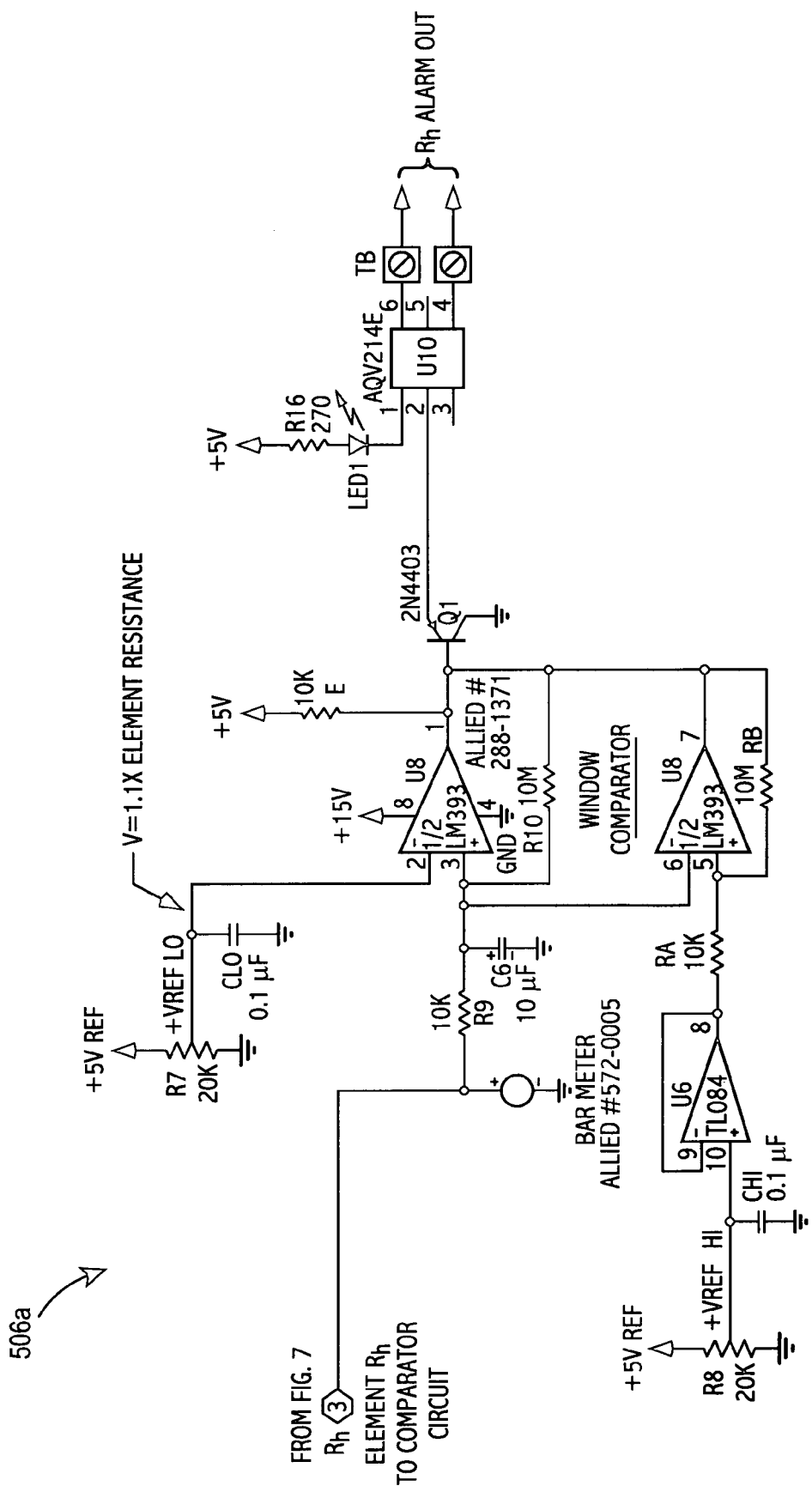
FIG. 8A is a schematic diagram of a portion of decision making circuitry in accordance with an embodiment of the present invention.
Figure 8B:
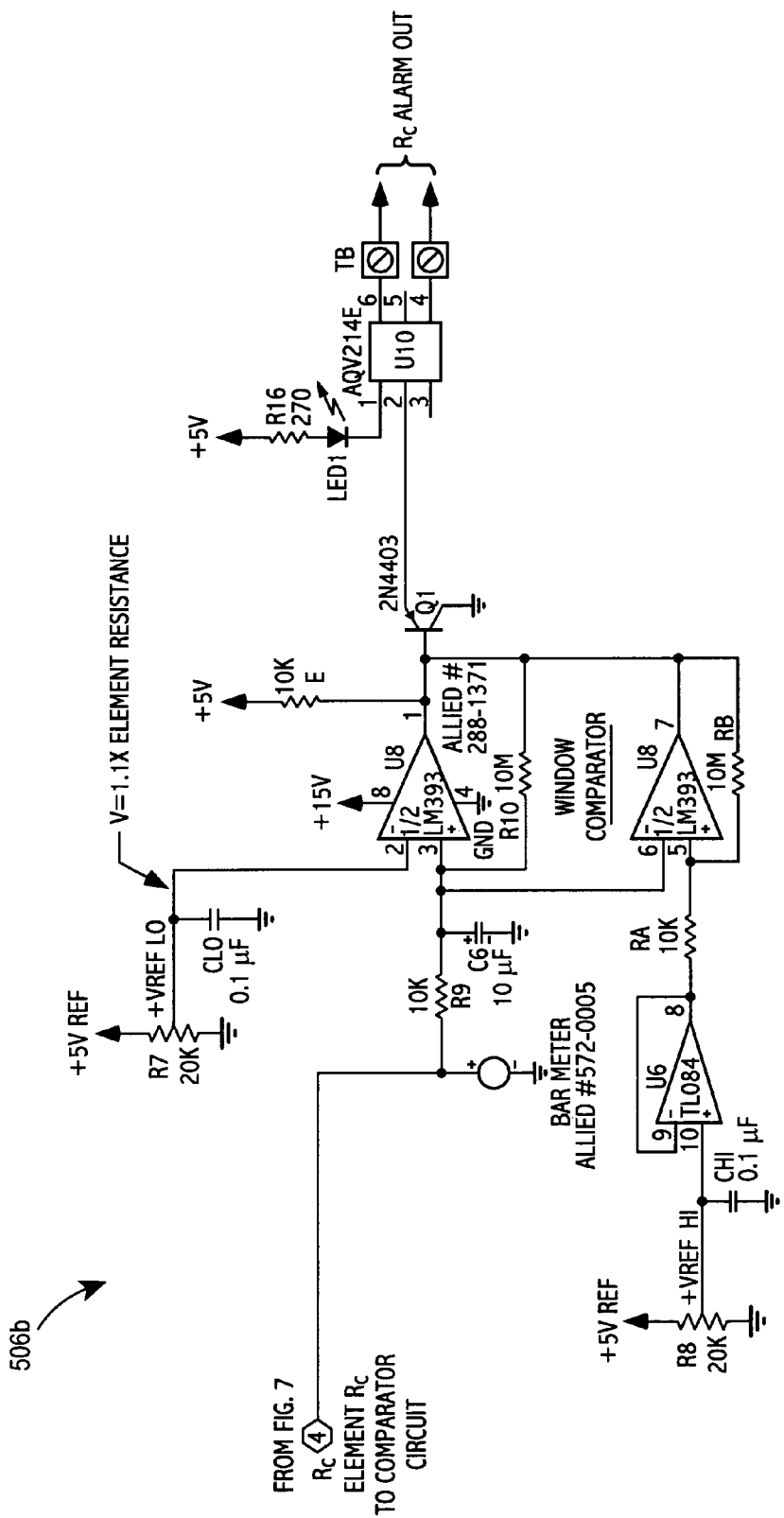
FIG. 8B is a schematic diagram of a portion of decision making circuitry in accordance with an embodiment of the present invention.
Figure 8C:
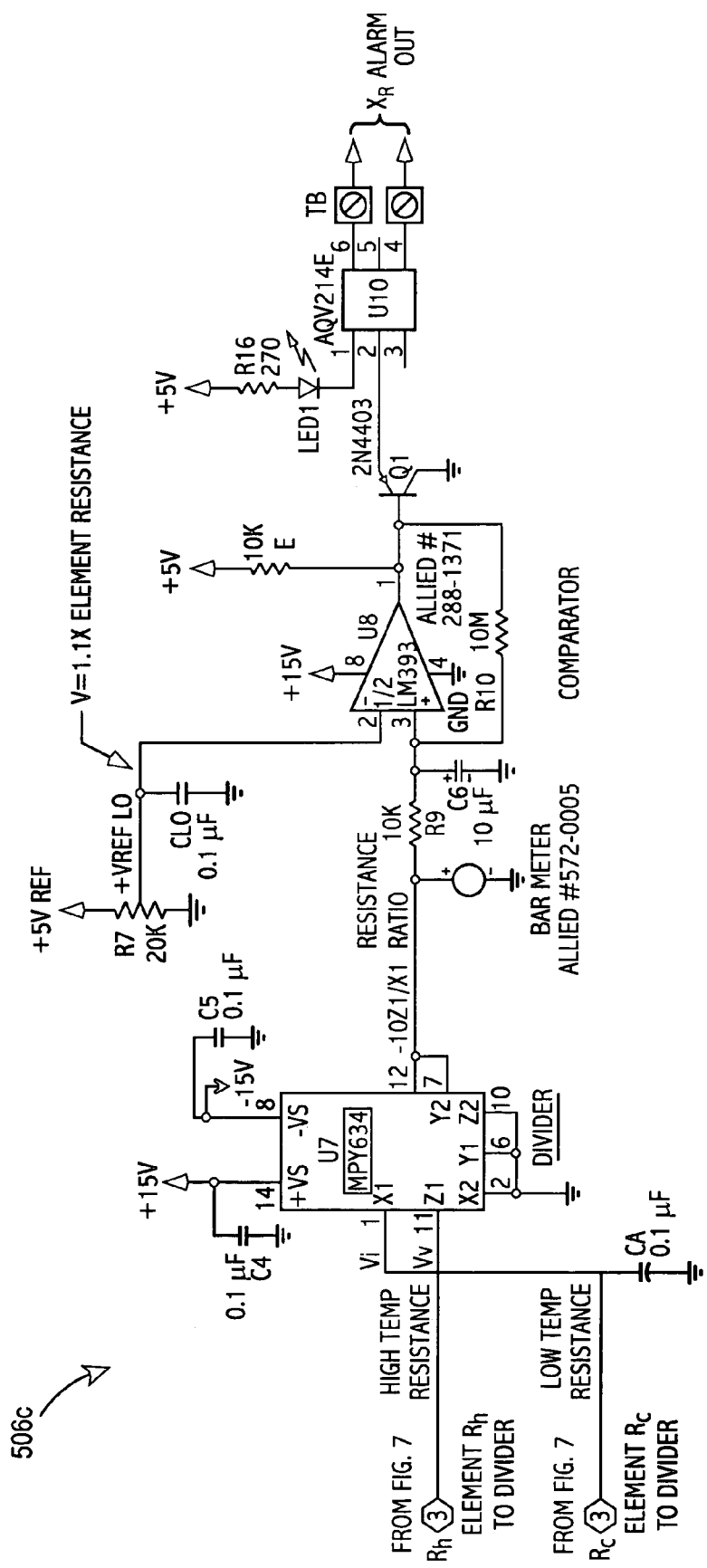
FIG. 8C is a schematic diagram of a portion of decision making circuitry in accordance with an embodiment of the present invention.

The sample and hold circuitry 504 shown in FIG. 7 is a digital sample and hold circuit, which converts an analog signal (received by way of Node 2) to digital signals for storing by way of an analog-to-digital converter (ADC). The digitized values for the heating element resistances are stored, and analog versions of the resistances are output by way of the digital-to-analog converters (DACs) to the decision making circuitry 506 via Nodes 3 and 4, which are also shown in FIGS. 8A, 8B, and 8C. Instantaneous values are stored when the "SCR on" signal is active and the appropriate R-Qual signal is input (unless, of course, the R-Qual module is optionally not used).

FIGS. 8A, 8B, and 8C show schematic diagrams of portions of the decision making circuitry 506a, 506b, and 506c, respectively. For example, the portion of the decision making circuitry 506a shown in FIG. 8A receives hot resistance $R_h$ information via Node 3 from the dual digital sample and hold circuitry 504 shown in FIG. 7. A dual window comparator is used to compare current values of $R_h$ to a pre-determined alarm threshold, and a mechanism is provided whereby an alarm can be activated if the values for $R_h$ reach a critical level. For example, a pre-determined alarm state for the hot resistance $R_h$ can be determined to indicate a critical failure mode, or other problems associated with either the monitoring circuitry, or the heating element being monitored.

Similarly, the portion of the decision making circuitry 506b shown in FIG. 8B receives cold resistance $R_c$ information via Node 4 from FIG. 7. This information is used by the dual window comparator shown in FIG. 8B in schematic form, to determine if a predetermined alarm condition has been reached, or if a predetermined threshold for the cold resistance value $R_c$ has been exceeded. If it is determined by the decision making circuitry 506b shown in FIG. 8B that such an alarm condition exists, an alarm can be activated regarding the cold resistance $R_c$.

The portion of the decision making circuitry 506c shown in FIG. 8C utilizes a divider to accept as inputs the hot resistance $R_h$ via Node 3 from FIG. 7 and the cold resistance $R_c$ via Node 4 from FIG. 7, and calculates the resistance ratio $X_R$. As previously discussed, a threshold of an acceptable limit for the resistance ratio $X_R$ can be predetermined, and the circuitry provided in FIG. 8C provides the ability to activate an alarm once this predetermined threshold has been exceeded. According to an embodiment of the present invention, the circuitry shown in the schematic diagram of FIG. 8C determines that an alarm condition has been reached for the resistance ratio $X_R$ if a high limit value for that variable has been exceeded. However, those skilled in the art will recognize that, as with the resistance values discussed in connection with FIGS. 8A and 8B, a dual window comparator could also be used for determining an alarm condition for the resistance ratio $X_R$, if desired.

The status display panel 508 shown in FIG. 5 can be used to display any of the alarm conditions associated with the resistance values or the resistance ratio values discussed in connection with FIGS. 8A, 8B, and 8C. This status display panel could be a variety of well known display types, such as light emitting diodes (LEDs), or more complicated display systems, such as a CRT monitor or LCD screen, displaying a read out, which could take many forms, including but not limited to, bar graphs, pie charts, numerical data displays, and the like.

The R-Qual module 510 shown in FIG. 5 as an optional addition to the impedance monitor 500, receives temperature input information, and provides quality information regarding the hot and cold temperature resistance values, such that an evaluation can be made regarding the quality of the values of $R_h$ and $R_c$, and whether these values can be measured and stored as accurate values. For example, the R-Qual module 510 can be used to indicate that the heating element's temperature is stable, or similarly that some other condition has been met that indicates the resistance values can be accurately measured. In accordance with an embodiment of the present invention, the R-Qual signal can be processed externally by a processor not shown. For example, if temperature stability is used as a condition for generating the signal, the R-Qual signal could be generated by a processor within the temperature controller. Those skilled in the art, however, will recognize that such processing could take place in a number of suitable locations, and need not be limited to a single location, either internal or external to the R-Qual module 510.

It will be understood by those skilled in the art that the circuitry shown and described in connection with the impedance monitor 500 and its schematic diagrams shown in FIGS. 6, 7, 8A, 8B, and 8C, is merely exemplary and various embodiments of the present invention can depart significantly from the circuitry shown therein. For example, the sample and hold circuitry 504 shown in FIG. 7 uses simple converters for converting and storing data (i.e., an ADC and a DAC). However, it is anticipated that a microcontroller having much greater functionality can be used in a sample and hold component 504 in place of or in addition to simple converters, such as the types shown in FIG. 7. Additionally, the functionality of much or all of the entire impedance monitor 500 shown in FIG. 5 could potentially be embedded in a microcontroller, as an embedded system therein. Moreover, a variety of indicators such as light emitting diodes (LEDs), electrical signals, sounds, and so forth, can be used to provide notification to a decision making authority that a threshold has been reached or exceeded, as determined by the decision making authority 506, and the status display panel is merely one option for such notification.

As discussed above, it is anticipated that a microcontroller can form a part of the sample and hold component 504 of the impedance monitor 500. Such an addition would be advantageous as the microcontroller could perform calculations and extrapolations of data. For example, such a microcontroller could be used to predict the remaining useful lifetime of a heating element based upon current measurements, calculations, and extrapolation algorithms. Additionally, other calculations could be taken into account and utilized by way of a microcontroller, such as probabilistic or heuristic algorithms, and so forth.

It will be understood by those skilled in the art that in practical situations, cooling the heating element to a cold level, or level of ambient temperature, may not be possible. Thus, it is anticipated that for the sake of efficiency and maximum production or "uptime," a furnace, and thus a heating element, may only be cooled to a temperature level that facilitates the required maintenance for the heating element and/or furnace. Thus, in practice the measurement of the cold temperature resistance $R_c$ may not be an exact measure, but can be taken from data previously determined, according to the make up of the alloy of the heating element. Additionally, because of the difficulty in cooling the heating element to ambient temperature with any frequency, the cold resistance $R_c$ of the heating element may require extensive modeling and measurement prior to use within the system. Moreover, it will be recognized by those skilled in the art that additional measurements, such as temperature measurements (i.e., maximum and minimum temperatures, etc.), can be used for increasing the accuracy in the model used by embodiments of the present invention to determine aluminum depletion. For example, instantaneous temperatures and corresponding instantaneous resistance values could be periodically measured over the lifetime of any heating element to update the model used for characterization of that element.

The presently disclosed embodiments are considered in all respects to be illustrative and not restrictive. The present invention can be embodied in other forms not disclosed herein, which do not depart from the spirit of the scope of the appended claims. The scope of the invention is indicated by the appended claims rather than the foregoing description, and all changes that come within the meaning and range of equivalents thereof are intended to be embraced therein.

What is claimed is:

1. A method for monitoring the condition of a material, comprising:

determining a reference baseline for at least two characteristics of a material;

monitoring the at least two characteristics characteristic of the material across time and/or temperature;

comparing the monitored characteristics against the reference baseline; and initiating a signal when a difference between the monitored characteristics and the reference baseline reaches or exceeds a predetermined value, wherein the difference between the monitored two or more characteristics and the reference baseline is caused by one or more of elongation of the material, a metallurgical change in a composition of the material, and a reduction in a cross-sectional area of the material.

2. The method according to claim 1, wherein the material is formed into a heating element.

3. The method according to claim 1, wherein the reference baseline is a geometric model of the condition of the material.

4. The method according to claim 1, wherein the monitored characteristics are representative of the condition of the material.

5. The method according to claim 1, wherein one of the characteristics is an electrical resistance of the material.

6. The method according to claim 1, wherein one of the characteristics is a voltage value.

7. The method according to claim 1, wherein one of the characteristics is a current value.

8. The method according to claim 1, wherein one of the characteristics is a temperature value.

9. The method according to claim 1, wherein monitoring is performed over a predetermined temperature range.

10. The method according to claim 9, wherein monitoring is performed over a temperature range of 20° C. to 1400° C.

11. The method according to claim 1, wherein monitoring is performed without shutting down the chamber in which the material is located.

12. The method according to claim 1, wherein monitoring the characteristics of the material is performed by measuring an electrical resistance of the material.

13. The method according to claim 1, wherein the difference between the monitored characteristics and the reference baseline is caused by elongation of the material.

14. The method according to claim 1, wherein the difference between the monitored characteristics and the reference baseline is caused by the metallurgical change in the composition of the material.

15. The method according to claim 1, wherein the difference between the monitored characteristics and the reference baseline is caused by the reduction in the cross-sectional area of the material.

16. The method according to claim 1, wherein the difference is caused by changes in the two or more characteristics and wherein a degree of change in any characteristic is not equal to a degree of change in one or more of the other monitored characteristics.

17. The method according to claim 1, wherein the material is a wire heating element comprised of an alloy of approximately 72.2% iron, 22.0% chromium, and 5.8% aluminum.

18. The method according to claim 17, wherein the predetermined value is indicative of a metallurgical change in the material, comprising a change in the aluminum content to less than 3.0% of the alloy.

19. The method according to claim 1, wherein the baseline reference and the monitored characteristic are converted to a graphical representation, and wherein the comparison between the monitored characteristic and the reference baseline is a geometric comparison.

20. The method according to claim 1, wherein the signal is initiated when the difference reaches a predetermined value.

21. The method according to claim 1, wherein the initiated signal is sent to a decision making authority.

22. The method according to claim 1, including detecting degradation or failure of the material based on a sudden change in the monitored characteristic.

23. A method for monitoring the condition of a heating element, comprising:
   determining a first graphical representation of a characteristic of a heating element as a reference baseline;
   setting a threshold level of graphical change for the characteristic;
   collecting data reflecting the condition of the characteristic of the heating element material after an interval;
   converting the collected data to a second graphical representation;
   comparing the difference between the first and second graphical representations against the threshold level of graphical change; and
   sending a signal to a decision making authority when the difference reaches or exceeds the threshold level,
   wherein the threshold level is set such that a signal is sent to the decision making authority when the alloy reaches a composition having approximately 2.5% of aluminum.

24. The method according to claim 23, wherein the heating element has an initial alloy composition of approximately 72.2% iron, 22.0% chromium, and 5.8% aluminum.

25. The method according to claim 23, wherein the collected data comprises the resistance measurements of the heating element.

26. The method according to claim 23, wherein comparing is performed as a geometric comparison.

27. An apparatus for monitoring the condition of the material, comprising:
   means for determining an initial composition of a material as a reference baseline at an initial time;
   means for collecting data reflecting a subsequent composition of the material after a specified time interval;
   means for setting a threshold level of change in the subsequent composition from the initial composition;
   means for monitoring a change in the composition of the material after the interval has passed; and
   means for sending a signal to a decision making authority when the monitored change has reached or exceeded the threshold level.

28. The apparatus according to claim 27, wherein the means for setting the initial composition sets a resistance baseline for a material comprising approximately 72.2% iron, 22.0% chromium and 5.8% aluminum.

29. The apparatus according to claim 27, wherein the threshold level comprises a level corresponding to the composition of the material containing approximately 2.5% of aluminum.

30. The apparatus according to claim 27, wherein the means for collecting data comprises a microcontroller.

31. The apparatus according to claim 27, wherein the means for collecting data comprises a sensing mechanism for sensing conditions of a heating element.

32. The apparatus according to claim 31, wherein the sensing mechanism senses electrical characteristics of a heating element.

33. The apparatus according to claim 27, wherein the means for setting sets a threshold level corresponding to a normalized resistance curve from 1.0 to 1.27 across a temperature range of approximately 20° C. to 1400° C.

34. The apparatus according to claim 27, wherein the means for monitoring comprises a microcontroller.

35. The apparatus according to claim 27, further comprising a decision making authority for responding to the means for sending, once the threshold level has been reached or exceeded.

36. The apparatus according to claim 35, wherein the decision making authority comprises a microcontroller.

* * * * *